(12) United States Patent
Kim

(10) Patent No.: US 7,728,043 B2
(45) Date of Patent: Jun. 1, 2010

(54) METHODS FOR TREATMENT OF BETA-AMYLOID PROTEIN-INDUCED OCULAR DISEASE

(76) Inventor: Darrick S. H. L. Kim, 834 Pinehurst La., Schaumburg, IL (US) 60193

( * ) Notice: Subject to any disclaimer, the term of this patent is extended or adjusted under 35 U.S.C. 154(b) by 925 days.

(21) Appl. No.: 11/287,080

(22) Filed: Nov. 23, 2005

(65) Prior Publication Data

US 2006/0148905 A1    Jul. 6, 2006

Related U.S. Application Data

(63) Continuation-in-part of application No. 11/128,638, filed on May 13, 2005, now Pat. No. 7,279,501, which is a continuation of application No. 11/084,316, filed on Mar. 18, 2005, now Pat. No. 7,282,523, which is a continuation of application No. 10/111,039, filed as application No. PCT/US00/41436 on Oct. 23, 2000, now Pat. No. 6,887,898.

(60) Provisional application No. 60/161,145, filed on Oct. 22, 1999, provisional application No. 60/739,797, filed on Nov. 23, 2005.

(30) Foreign Application Priority Data

Oct. 23, 2000   (EP) .................................. 00986827

(51) Int. Cl.
*A61K 31/12* (2006.01)
(52) U.S. Cl. ....................... 514/678; 514/912
(58) Field of Classification Search ................. 514/679, 514/912
See application file for complete search history.

(56) References Cited

U.S. PATENT DOCUMENTS

| 5,089,636 A | 2/1992 | Kwak et al. |
| 5,266,344 A | 11/1993 | Mimura et al. |
| 5,587,358 A | 12/1996 | Sukigara et al. |
| 5,861,415 A * | 1/1999 | Majeed et al. ............... 514/321 |

(Continued)

FOREIGN PATENT DOCUMENTS

JP        02-193930        7/1990

(Continued)

OTHER PUBLICATIONS

Artico et al., "Geometrically and Confromationally Restrained Cinnamoyl Compounds as Inhibitors of HIV-1 Integrase: Synthesis, Bioligical Evaluation, and Molecular Modeling," *J. Med. Chem.*, 41:3948-3960 (1998).

(Continued)

*Primary Examiner*—Taylor Victor Oh
(74) *Attorney, Agent, or Firm*—Marshall, Gerstein & Borun LLP

(57) ABSTRACT

The invention provides methods for treating beta-amyloid protein-involved ocular disease including age-related macular degeneration and glaucoma, pharmaceutical compositions and compounds useful for the same, and the use of these compounds for the manufacture of a medicament for treating the same. More particularly, the invention relates to the use of natural product compounds isolated from *Curcuma* sp., *Zingiber* sp., *Ginkgo biloba*, *Salvia* sp., and *Rosmarinus* sp. and synthetic chemical analogues thereof, for the treatment of a beta-amyloid protein-involved ocular disease.

5 Claims, 11 Drawing Sheets

U.S. PATENT DOCUMENTS

| | | | |
|---|---|---|---|
| 6,887,898 | B1 | 5/2005 | Kim |
| 2004/0101578 | A1 | 5/2004 | Kim et al. |

FOREIGN PATENT DOCUMENTS

| | | |
|---|---|---|
| JP | 07206669 | 8/1995 |
| JP | 08-040970 | 2/1996 |
| JP | 11246398 | 9/1999 |
| WO | WO 97/03674 | 2/1997 |
| WO | WO 98/51302 | 11/1998 |
| WO | WO 00/70949 | 11/2000 |
| WO | WO 01/30335 A2 | 5/2001 |

OTHER PUBLICATIONS

Beard, et al., "Nonsteroidal Anti-Inflammatory Drug Use and Alzheimer's Disease: A Case-Control Study in Rochester, MN 1980-1984," *Mayo Foundation for Medical Education and Research* 73(10), 951-955 (1998).

Behl et al., "Hydrogen Peroxide Mediates Amyloid β Protein Toxicity," *Cell* 77, 817-827 (1994).

Carr, et al., "Current Concepts in the Pathogenesis of Alzheimer's Disease," *The American Journal of Medicine*, 103(3A), 3S-10S (1997).

Chang et al., "The Effect of Chinese Medicinal Herb *Zingiberis rhizoma* Extract on Cytokine Secretion by Human Peripheral Blood Mononuclear Cells," *J. Ethnopharmacology*, 48:13-19 (1995).

Clostre, "*Ginkgo biloba* extract (EGb 761): A State of Art at the Dawn of the Third Millennium," Annales Pharmaceutiques Francaises, 57, No. Suppl. 1:1S8-1S88 (1999).

Conney et al., "Inhibitory Effect of Curcumin and Some Related Dietary Compounds on Tumor Promotion and Arachidonic Acid Metabolism in Mouse Skin," *Advances in Enzyme Regulation*, Proceedings of the Thirty-First Symposium on Regulation of Enzyme Activity and Synthesis in Normal and Neoplastic Tissues held at Indiana University School of Medicine, Weber, ed., vol. 31, pp. 385-396 (1991).

Cuajungco, et al., "Zinc Metabolism in the Brain: Relevance to Human Neurodegenerative Disorders," *Neurobiology of Disease* 4, 137-169 (1997).

Davis, et al., "The Amyloid Beta-Protein of Alzheimer's Disease is Chemotactic for Mononuclear Phagocytes," *Biochemical and Biophysical Research Communications* 189(2) 1096-1100 (1992).

Friedlich et al., "Involvement of Free Oxygen Radicals in β-Amyloidosis: An Hypothesis," *Neurobiology of Aging* 15(4), 443-455 (1994).

Gellerman et al., "Antimicrobial Effects of Anacardic Acids," *Canadian Journal of Microbiology*, 15:1219-1223 (1969).

Ghanta et al., "A Strategy for Designing Inhibitors of β-Amyloid Toxicity," *The Journal of Biological Chemistry* 271(47), 29525-29528 (1996).

Goedert, "Tau protein and the neurofibrillary pathology of Alzheimer's disease," *TINS* 16(11) 460-465 (1993).

Green et al., "Nuclear Estrogen Receptor-Independent Neuroprotection by Estratrienes: A Novel Interaction with Glutathione," *Neuroscience* 84(1), 7-10 (1998).

Haass et al., "Cellular Processing of β-Amyloid Precursor. Protein and the Genesis of Amyloid β-Peptide," *Cell* 75 10-39-1042 (1993).

Harkany et al., "Cholinotoxic effects of β-amyloid $_{(1-42)}$ peptide on cortical projections of the rat nucleus *Basalis magnocellularis*," *Brain Research* 695, 71-75 (1995).

He et al., "High-Performance Liquid Chromatography-Electrospray Mass Spectrometric Analysis of Pungent Constituents of Ginger," *J. Chromatography A*, 796:327-334 (1998).

Hefti, "Development of Effective Therapy for Alzheimer's Disease Based on Neurotrophic Factors," *Neurobiology of Aging* 15(2), S193-S194 (1994).

Henderson, "The epidemiology of estrogen replacement therapy and Alzheimer's disease," *American Academy of Neurology* 48(5), S. 7, 275-355 (1997).

Hensley et al., "A model for β-amyloid aggregation and neurotoxicity based on free radical generation by the peptide: Relevance to Alzheimer disease," *PNAS USA* 91, 3270-3274 (1994).

Hertel et al., "Inhibition of the electrostatic interaction between β-amyloid peptide and membranes prevents β-amyloid-induced toxicity," *PNAS USA* 94, 9412-9417 (1997).

Hidalgo et al., "Determination of the Carnosic Acid Content in Wild and Cultivated *Rosmarinus officinalis*," *J. Agric. Food. Chem* 46, 2624-2627 (1998).

Hiserodt et al., "Isolation of 6-, 8-, and 10-Gingerol from Ginger Rhizome by HPLC and Preliminary Evaluation of Inhibition of *Mycobacterium avium* and *Mycobacterium tuberculosis*," *J. Agric. Food Chem.*, 46:2504-2508 (1998).

Hopia et al., "Effect of Different Lipid Systems on Antioxidant Activity of Rosemary Constituents Carnosol and Carnosic Acid with and without α-Tocopherol," *J. Agric. Food Chem* 44, 2030-2036 (1996).

Hoshi et al., "Nontoxic Amyloid β Peptide $_{1-42}$ Suppresses Acetylocholine Synthesis," *The Journal of Biological Chemistry* 272(4), 2038-2041 (1997).

Huang et al., "Novel Bipheny Ether Liganans from the Rhizomes of *Curcuma chuanyujin*," *Chem. Pharm. Bull*, 48(8):1228-1229 (2000).

Ihara et al., "Phosphorylated Tau Protein Is Integrated into Paired Helical Filaments in Alzheimer's Disease," *J. Biochem* 99, 1807-1810 (1986).

Itokawa et al., "Antitumor Principles from *Ginkgo biloba* L.," *Chem. Pharm.Bull.*, 35(7):3016-3020 (1987).

Jitoe et al., "Antioxidant Activity of Tropical Ginger Extracts and Analysis of the Contained Curcuminoids," *J. Agric. Food Chem* 40, 1337-1340 (1992).

Jung et al., "Effects of Curcumin on the Microglial Activation," *Yakhak Hoeji*, 44(5):448-454 (2000).

Kelloff et al., "Chemopreventive Drug Development: Perspectives and Progress," *Cancer Epidemiol. Biomarkers & Prev.*, 3:85-98 (1994).

Khopde et al., "Free Radical Scavenging Ability and Antioxidant Efficiency of Curcumin and its Substituted Analogue," *Biophysical Chemistry*, 80:85-91 (1999).

Kiergis et al., "Activation of Macrophages by Alzheimer β Amyloid Peptide," *Biochemical and Biophysical Research Communications* 199(2), 984-991 (1994).

Kihara et al., "Stimulation of α4β2 nicotinic acetylcholine receptors inhibits β-amyloid toxicity," *Brain Research* 792, 331-334 (1998).

Kikuzaki et al., "Antioxidant Effects of Some Ginger Constituents," *Journal of Food Science* 58(6), 1407-1410 (1993).

Kim et al.,"Inhibition of β-Amyloid Neurotoxicity in PC12 Cells by CLZ-1, CLZ-2 and CLZ-3 Isolated From *Curcuma longa*, Zingiberaceae: An Approach Toward A Rational Drug Discovery of Anti-Alzheimer Disease," *Society for Neuroscience Abstracts*, 24(1-2):1457 (1998).

Kim et al., "Curcuminoids from *Curcuma longa* L. (Zingiberaceae) that Protect PC12 Rat pheochromocytoma and Normal Human Umbilical Vein Endothelial Cells from βA(1042) Insult," *Neuroscience Letters*, 303:57-61 (2001).

Kim et al., "Shogaols from *Zingiber officinale* Protect IMR32 Human Neuroblastoma and Normal Human Umbilical Vein Endothelial Cells from β-Amyloid (25-35) Insult," *Letter ... Planta Med* 2002 68, 375-376 (2002).

Kumar et al., "The Acute Neurotoxic Effect of β-Amyloid on Mature Cultures of Rat Hippocampal Neurons is Attenuated by the Anti-Oxidant U-78517F," *Intern. J. Neuroscience* 79, 185-190 (1994).

Kuner et al., "β-Amyloid Binds to p75$^{NTR}$ and Activates NFκB in Human Neuroblastoma Cells," *J. Neuroscience Res.*, 54:798-804 (1998).

Lahiri et al., "Tacrine Alters the Secretion of the Beta-Amyloid Precursor Protein in Cell Lines," *Journal of Neuroscience Research* 37: 777-787 (1994).

Larner, "Neurite Growth-inhibitory Properties of Amyloid Beta-peptides in vitro: A Beta 25-35, but not A Beta 1-40, is Inhibitory," *Neurosci Res. Commun.* 20(3): 147-155 (1997).

Lee et al., "Induction of Apoptosis in HL-60 Cells by Pungent Vanilloids, [6]-gingerol and [6]-paradol," *Cancer Letters*, 134:163-168 (1998).

Lim et al., "Prevention of LTP deficits in Alzheimer Ttransgenic HuAPPSw Mice Using a Phenolic Anti-oxidant/anti-inflammatory Compound," *Society for Neuroscience Abstracts*, 26(1-2):Abstract No. 763.9 (2000).

Lorenzo et al., "Amyloid Fibril Toxicity in Alzheimer's Disease and Diabetes$^{a}$", *Annals New York Academy of Sciences*: 89-95.

Lucca et al., "Influence of cell culture conditions on the protective effect of antioxidants against β-amyloid toxicity: studies with lazaroids," *Brain Research* 764: 2930298 (1997).

Manelli et al., "β-Amyloid-Induced Toxicity in Rat Hippocampal Cells: In Vitro Evidence for the Involvement of Free Radicals," *Brain Research Bulletin* 18(6): 569-576. (1995).

Mattson, "Neuroprotective Signal Transduction: Relevance to Stroke," *Neurosci Biobehav Rev* 21(2): 193-206 (1997).

Maurer et al., "Clinical Efficacy of *Ginkgo biloba* Special Extract EGb 761 in Dementia of the Alzheimer Type," *J. Psychiat. Res.*, 31(6):645-655 (1997).

Maurice et al., "Amnesia induced in mice by centrally administered β-amyloid peptides involves cholinergic dysfunction, *Brain Research* 706:181-193 (1996).

Meda et al., "Activation of microglial cells by beta-amyloid protein and interferon-gamma," *Nature* 374(6523):647-650 (1995).

Morimoto et al., "Sterische Struktur der Giftstoffe aus dem Fruchtfleisch on *Ginkgo biloba* L.," *Chem. Pharm. Bull.*, 16(11):2282-2286 (1968).

Müller et al. "Protection of Flupertine on β-Amyloid-lnduced Apoptosis in Neuronal Cells In Vitro: Prevention of Amyloid-Induced Glutathione Depletion," *Journal of Neurochemistry* 68(6):2371-2377 (1997).

Nagabhushan et al., "Mutagenicity Of Gingerol And Shogaol And Antimutagenicity Of Zingerone In *Salmonella*/Microsome Assay," *Cancer Letters*, 36:221-233 (1987).

Nakatani et al., "A New Diterpene Lactone, Rosmadial, from Rosemary," *Agric. Biol. Chem.* 47(2):353-358 (1983).

Nakayama, "Strategy of Chemical Modification to Free Radical Scavengers for Suppression of Hydrogen Peroxide-Induced Cytotoxicity," *Food Factors Cancer Prev., Int. Conf.*, 1995, pp. 642-646 (1997).

Niijima et al., "Effect of Oral Administration of *Pinellia ternata*, *Zingiberis rhizoma* and Their Mixture on the Efferent Activity of the Gastric Branch of the Vagus Nerve in the Rat," *Neuroscience Letters*, 258:5-8 (1998).

Nurfina et al., "Synthesis of Some Symmetrical Curcumin Derivatives and Their Anti-Inflammatory Activity," *Eur. J. Med. Chem.*, 32:321-328 (1997).

Osawa et al., "Antioxidative Activity of Tetrahydrocurcuminoids," *Biosci. Biotech. Biochem.*, 59(9):1609-1612 (1995).

Park et al., "Discovery of Natural Products from *Curcuma longa* that Protect Cells from Beta-Amyloid Insult: A Drug Discovery Effort Against Alzheimer's Disease," *Journal of Natural Products* 65(9):1227-1231 (2002).

Parnetti et al., "Cognitive Enhancement Therapy for Alzheimer's Disease," *Drugs* 53(5): 752-768 (1997).

Pasinetti et al., "Cyclooxygenase-2 Expressiosn is Increased in Frontal Cortex of Alzheimer's Disease Brain," *Neuroscience* 87(2):319-3224 (1998).

Pike et al., "Neurodegeneration Induced by β-Amyloid Peptides in vitro: The Role of Peptide Assembly State," *The Journal of Neuroscience* 13(4) 1676-1687 (1993).

Pike et al., "β-Amyloid Neurotoxicity In Vitro: Evidence of Oxidative Stress but Not Protection by Antioxidants," *Journal of Neurochemistry* 69(4):1601-1611 (1997).

Pollack et al., "Sulfonated dyes attenuate the toxic effects of β-amyloid in a structure-specific fashion," *Neuroscience Letters* 197: 211-214 (1995).

Prasain et al., "Inhibitory Effect of Diarylheptanoids on Nitric Oxide Production in Activated Murine Macrophages," *Biol. Pharm. Bull.*, 21(4):371-374 (1998).

Preston et al., Toxic effects of β-amyloid(25035) on immortalized rat brain endothelian cell: protection by carnosine, homecarnosine and β-alanine, *Neuroscience Letters* 242: 105-108 (1998).

Puttfarcken et al., "Inhibition of Age-Induced β-Amyloid Neurotoxicity in Rat Hippocampal Cells," *Experimental Neurology* 138: 73-81 (1996).

Ruby et al., "Anti-tumor and Antioxidant Activity of Natural Curcuminoids," *Cancer Letters*, 94: 79-83 (1995).

Schulick, Ginger, *Common Spice & Wonder Drug*, $3^{rd}$ Edition, Hohm Press, pp. 1-166 (1996).

Seidl et al., "Evidence against increased glycoxidation in patients with Alzheimer's disease," *Neuroscience Letters* 232, 49-52 (1997).

Seiger et al., "Intraracial infusion of purified nerve growth factor to an Alzheimer patient: the first attempt of a possible future treatment strategy," *Behavioral Brain Research* 57:255-261 (1993).

Shastry, "Molecular Genetics of Familial Alzheimer Disease," *The American Journal of the Medical Sciences*, 315(4), 266-272 (1998).

Skolnick, "Old Chinese Herbal Medicine Used for Fever Yields Possible New Alzheimer Disease Therapy," *JAMA*, 277(10):776 (1997).

Soliman et al., "In vitro Attenuation of Nitric Oxide Production in C6 Astrocyte Cell Culture by Various Dietary Compounds," *Proc. Soc. Exper. Biol. Med.*, 218(4):390-397 (1998).

St-George-Hyslop et al., "Antibody clears senile plaques," *Nature* 400:116-117 (1999).

Suekawa et al., "Pharmacological Studies On Ginger. I. Pharmacological Actions Of Pungent Constituents, (6)-Gingerol and (6)-Shogaol," *J. Pharm Dyn.*, 7:836-848 (1984).

Tatton et al., "Modulation of gene expression rather than monoamine oxidase inhibition: (-)-Deprenyl-related compounds in controlling neurodegeneration," *Neurology* 47(6) S. 3: 1715-1835 (1996).

Thomas et al., "Beta-Amyloid-mediated vasoactivity and vascular endothelial damage," *Nature* 380(6570):168-171 (1996).

Trojanowski et al., "Paired Helical Filament τ in Alzheimer's Disease-The Kinase Connection," *American Journal of Pathology* 144(3) 449-453 (1994).

Trojanowski et al. "Phosphorylation of paired helical filament tau in Alzheimer;s disease neurofibrallary lesions: focusing on phosphates," The FASB Journal 9:1571-1576 (1005).

Venkateshwarlu, "Cyclo-Oxygenase Inhibityors From Spices," *Indian Drugs*, 34(8):427-432 (1997).

Yaar et al., "Binding of β-Amyloid to the p75 Neurotrophin Receptor Induces Apoptosis," *The Journal of Clinical Investigation* 100(9): 2333-2340 (1997).

Yan et al., "RAGE and amyloid-β peptide neurotoxicity in Alzheimer's disease," *Nature* 382 (1996).

Yoshikawa et al., "Qualitative and Quantitative Analysis of Bioactive Principles in *Zingiberis rhizoma* by Means of High Performance Liquid Chromatography and Gas Liquid Chromatography. On the Evaluation of *Zingiberis rhizoma* and Chemical Change of Constituentsduring *Zingiberis rhizoma* Processing," Regular Articles, *Yakugaku Zasshi*, 113:-307-315 (1993).

Zhou et al., "Actions of Neurotoxic β-Amyloid on Calcium Homeostasis and Viability of PC12 Cells are Blocked by Antioxidants but not by Calcium Channel Antagonists," *Journal of Neurochemistry* 67(4): 1419-1425 (1996).

International Search Report dated Mar. 8, 2002 for International Application No. PCT/US00/41436.

Written Opinion dated Mar. 18, 2002 for International Application No. PCT/US00/41436.

Locksley et al., "Perkin Transactions," *J. Chem. Soc.*, 23:3001-3006 (1972).

Bate et al., "Ginkgolid B inihibits the nuerotoxicity of prions or amyloid-β 1-42," *Journal of Neuroinflammation*, 1(4):1-8, (2004).

Dentchev et al., "Amyloid-β is found in drusen from some age-related macular degneration retinas, but not in drusen from normal retinas," *Molecular Vision*, 9:184-190 (2003).

European Search Report, dated Sep. 7, 2009, for European Application No. 06 77 3132.

Janciauskiene et al., "Alzheimer's peptide and serine proteinase inhibitors in glaucoma and exfoliation syndrome," Documenta Ophthalmologica 106, (2003).

Johnson et al., "The Alzheimer's Aβ-peptide is deposited at sites of complement activation in pathologic deposits associated wit aging and age related macular degeneration," *Neuroscience Research Institute*, 99(18): 11830-11835, (2002).

Kim et al., Shogaols from *Zingiber* officinal Protect IMR32 Human Neuroblastoma and Normal Human Umbilical Vein Endothelial Cells from β-Amyloid (25-35) Insult,: *Planta Med.*, 68:375-376 (2002).

Kim et al., "Side-chain length is important for shogaols in protecting neuronal cells from β-amyloid insult," *Bioorganic & Medicinal Chemistry Letters*, 14:1287-1289 (2004).

McKinnon, S., "Glaucoma: Ocular Alzheimer's Disease?" *Frontiers in Bioscience*, 8:s1140-1156 (2003).

Ono et al., "Curcumin Has Potent Anti-Amyloidogenic Effects for Alzheimer's β-Amyloid Fibrils In Vitro," *Jour. of Neuroscience Res.*, 75:742-750 (2004).

Park, S., "Discovery of Natural Products from Turmeric and Sage that Protect Cells Against Beta-Amyloid Insult," (2001).

Yao, "The *Ginkogo biloba* extract EGb 761 rescues the PC12 neuronal cells from βamyloid-induced cell death by inhibiting the formation of β-amyloid-derived diffusible neurotoxic ligands," *Brain Research*, 889:181-190 (2001).

* cited by examiner (1)

(3)

(4)

(6)

(7)

(8)

(9)

(10)

(27)

(28)

(11)

(12)

(13)

(14)

(15)

(16)

METHODS FOR TREATMENT OF BETA-AMYLOID PROTEIN-INDUCED OCULAR DISEASE

RELATED APPLICATIONS

This application is a Continuation-in-Part of U.S. patent application Ser. No. 11/128,638 filed May 13, 2005 which is a Continuation of U.S. patent application Ser. No. 11/084,316 filed Mar. 18, 2005 which is a Continuation of U.S. patent application Ser. No. 10/111,039 filed Apr. 19, 2002 now U.S. Pat. No. 6,887,898 which was the U.S. National Phase of International Patent Application Serial No. PCT/US00/41436 filed Oct. 23, 2000, which claims priority from European Patent Application No. 00986827.4, filed Oct. 23, 2000, which claims benefit of U.S. Provisional Patent Application Ser. No. 60/161,145 filed Oct. 22, 1999 the disclosures of which are hereby incorporated by reference. This application also claims benefit of U.S. Provisional Patent Application Ser. No. 60/690,812 filed Jun. 15, 2005 the disclosure of which is hereby incorporated by reference. This application also claims benefit of U.S. Provisional Patent Application Serial No. 60/739,797 filed Nov. 23, 2005 entitled "Synergistic Pharmaceutical Compositions Useful in Prevention and Treatment of Beta-Amyloid Protein-Induced Disease Including Sage and Rosemary Derived Compounds" the disclosure of which is hereby incorporated by reference.

BACKGROUND OF THE INVENTION

1. Field of the Invention

The invention relates to the use of natural product compounds isolated from plants, and synthetic chemical analogues thereof, for the prevention and treatment of beta-Amyloid protein-induced disease. Specifically, the invention relates to pharmaceutical compositions that protect neuronal cells from beta-Amyloid insult for use in preventing and treating beta-Amyloid protein-induced disease. More particularly the invention is directed to protection of retinal cells and other visual function related cells of the eyes from beta-amyloid involved pathology, in particular, glaucoma and age-related macular degeneration (AMD).

2. Description of Related Technology

Alzheimer's disease (AD) is the most common cause of progressive cognitive dysfunction. AD affects approximately four million Americans and causes more than 100,000 deaths each year, with a total annual cost approaching $100 billion. It is estimated that by the year 2020, 14 million Americans will be afflicted by the disease. See Carr et al., *Am J Med* 103, 3S (1997) and Shastry, *Am J Med Sci* 315, 266 (1998). Furthermore, AD has a profound effect on the millions of family members and other loved ones who provide most of the care for people having this disease. Unfortunately, the cure for AD has not yet been discovered.

The principal pathological characteristics of AD are senile plaques and neurofibrillary tangles (NTFs). Senile plaques are extracellular deposits principally composed of insoluble aggregates of beta-amyloid ($\beta A$), that are infiltrated by reactive microglia and astrocytes. See Seidl et al., *Neurosci. Lett* 232, 49 (1997), Yan et al., *Nature* 382, 685 (1997), Goedert, *Trends Neurosci* 16, 460 (1993), Haass et al., *Cell* 7, 1039 (1994), Trojanowski et al., *Am J Pathol* 144, 449 (1994), Davis et al., *Biochem Biophys Res Commun* 189, 1096 (1992), Pike et al., *Neuroscience* 13, 1676 (1993), Hensley et al., *Proc Natl Acad Sci USA* 91, 3270 (1994), Behl et al., *Cell* 77, 817 (1994), Meda et al., *Nature* 374, 647 (1995), and Klegeris et al., *Biochem Biophys Res Commun* 199, 984 (1994). Plaques are diffusely distributed throughout the cerebral cortex of AD patients, and are the neuropathologic hallmark of the disease. See Seidl et al., *Neurosci Lett* 232, 49 (1997), Yan et al., *Nature* 382, 685 (1997), Goedert, *Trends Neurosci* 16, 460 (1993), Haass et al., *Cell* 7, 1039 (1994) and Trojanowski et al., *Am J Pathol* 144, 449 (1994). These plaques or $\beta A$ fibril deposits are believed to be responsible for the pathology of a number of neurodegenerative diseases including, but not limited to, Alzheimer's disease. NTFs are intraneuronal accumulation of paired helical filaments composed mainly of an abnormal form of tau protein, that is a microtubule associated phosphoprotein which can promote microtubule formation. See Goedert, *Trends Neurosci* 16, 460 (1993), Haass et al., *Cell* 7, 1039 (1994) and Trojanowski et al., *Am J Pathol* 144, 449 (1994). In the AD brain, the tau protein in NFTs is hyperphosphorylated (See Ihara et al., *J Biochem* 99, 1807 (1986)), a condition which has been suggested to contribute to the destabilization of microtubule network, thereby impairing axonal network, and eventually causing neuronal death. See Trojanowski et al., *FASEB J* 9, 1570 (1995). NTFs occur primarily in medial temporal lobe structures (hippocampus, entorhinal cortex, and amygdala), and NTFs density appears to correlate with dementia severity.

Senile plaques and NTFs appear to be involved in cerebral amyloid angiopathy, consequent neuronal loss, and cerebral atrophy leading to dementia. Although research findings suggest that both plaques and NTFs are involved in disrupting nerve cell functions, the mechanisms that lead to the pathology are not clearly understood.

$\beta A$ has been suggested as one of the major causes of AD. $\beta A$ was shown to exert direct toxic effects on neurons and to inhibit neurite growth in vitro in a dose dependent manner. Thus, therapeutic approaches that can modulate $\beta A$ toxicity have been hypothesized to represent important methods for controlling the onset of AD. It is envisioned that if neuronal cells can be protected from $\beta A$/senile plaque-induced toxicity, the onset of AD may be delayed or prevented. Current pharmacological approaches related to AD preventive and neuroprotective interventions include antioxidant therapy (See Lucca et al., *Brain Res* 764, 293 (1997), Pike et al., *J Neurochem* 69, 1601 (1997), Manelli et al., *Brain Res Bull* 38, 569 (1995), Parnetti et al., *Drugs* 53, 752 (1997), Zhou et al., *J Neurochem* 67, 1419 (1996), Kumar et al., *Int J Neurosci* 79, 185 (1994), Preston et al., *Neurosci Lett* 242, 105 (1998), and Tatton et al., *Neurology* 47, S171 (1996)), acetylcholinesterase inhibitors (See Hoshi et al., *J Biol Chem* 272, 2038 (1997), Maurice et al., *Brain Res* 706, 181 (1996), Harkany et al., *Brain Res* 695, 71 (1995), and Lahiri et al., *J Neurosci Res* 37, 777 (1994)), nicotinic and muscarinic agonists (See Maurice et al., *Brain Res* 706, 181 (1996), and Kihara et al., *Brain Res* 792, 331 (1998)), estrogen (See Ihara et al., *J Biochem* 99, 1807 (1986), Henderson, *Neurology* 48 (5 Suppl. 7), S27 (1997), and Green et al., *Neuroscience* 84, 7 (1998)), nerve growth factor (NGF) (See Hefti, *Neurobiol Aging* 15 (Suppl 2), S193 (1994), and Seiger et al., *Behav Brain Res* 57, 255 (1993)), calcium channel blockers (See Zhou et al., *J Neurochem* 67, 1419 (1996) and Friedlich et al., *Neurobiol Aging* 15, 443 (1994)), Zinc (See Cuajungco et al., *Neurobiol Dis* 4, 137 (1997)), sulfonated compounds (See Pollack et al., *Neurosci Lett* 197 211 (1995) and Lorenzo, et al., *Ann NY Acad Sci* 777, 89 (1996)), triaminopyridine nonopiate analgesic drug (See Muller et al., *J Neurochem* 68, 2371 (1997)), low molecular lipophilic compounds that can activate neurotrophic factor signaling pathway (See Mattson, *Neurosci Biobehav Rev* 21, 193 (1997)), and non-steroidal anti-inflammatory drugs such as ibuprofen and aspirin (See Parnetti et al., *Drugs* 53, 752 (1997), Beard et al., *Mayo Clin Proc* 73, 951 (1998), and Pasinetti et al., *Neuroscience* 87, 319 (1998)). Of particular interest to the present invention is the observation that an anti-βA protein antibody was shown to clear senile plaques and protect mutant PDAPP mice from the onset of AD. See St George-Hyslop et al., *Nature* 400, 116 (1999).

The generation of reactive oxygen intermediates (ROS) through oxidative stress caused by βA has been suggested to be the major pathway of the βA-induced cytotoxicity. See Klegeris et al., *Biochem Biophys Res Comun* 199, 984 (1994) and Lucca et al., *Brain Res* 764, 293 (1997). Senile plaques have been shown to exert a cytotoxic effect on neurons by stimulating microglia to produce reactive oxygen species (ROS). See Seidl et al., *Neurosci Lett* 232, 49 (1997), Yan et al., *Nature* 382, 685 (1997), Goedert, *Trends Neurosci* 16, 460 (1993), Haass et al., *Cell* 7, 1039 (1994), Trojanowski et al., *Am J Pathol* 114, 449 (1994), Davis et al., *Biochem Biophys Res Commun* 189, 1096 (1992), Pike et al., *Neuroscience* 13, 1676 (1993), Hensley et al., *Proc Natl Acad Sci USA* 91, 3270 (1994), Behl et al., *Cell* 77, 817 (1994), Meda et al., *Nature* 374, 647 (1995) and Klegeris et al., *Biochem Biophys Res Commun* 199, 984 (1994). The damaging effect of ROS can be prevented by the free radical scavenging enzyme superoxide dismutase (SOD). See Thomas et al., *Nature* 380, 168 (1996) and Manelli et al., *Brain Res Bull* 38, 569 (1995).

Aging of synthetic βA for 7 to 14 days at 37° C. in modified Eagle's media was also demonstrated to cause neurotoxic free radical formation. See Friedlich et al., *Neurobiol Aging* 15, 443 (1994) and Puttfarcken et al., *Exp Neurol* 138, 73 (1996). However, aging PA in the presence of the media supplement B27, which contains antioxidants as well as other agents that provide protection against oxidative damage, has been shown to inhibited βA-induced neurotoxicity. See Thomas et al., *Nature* 380, 168 (1996) and Manelli et al., *Brain Res Bull* 38, 569 (1995).

In addition to βA peptide-induced ROS mediated neurotoxicity, βA peptide has been shown to cause neuronal cell death by stimulating microglial expression of tumor necrosis factor β (TNFβ). See Tarkowski et al., *Neurology* 54, 2077 (2000) and Barger et al., *Proc Natl Acad Sci USA* 92, 9328 (1995). The accumulation of βA peptide as neuritic plaques is known to be both trophic and toxic to hippocampal neurons, causing apoptosis or necrosis of the neurons in a dose dependent manner. βA peptide was demonstrated to induce these cellular effects by binding with a receptor for advanced glycation end products (RAGE) that was previously known as a central cellular receptor for advanced glycation endproducts. See Arancio et al., *EMBO J* 23, 4096 (2004), Huttunen et al., *J Biol Chem* 274, 19919 (1999), and Yan et al., *Nature* 382, 685 (1996). RAGE was suggested to mediate the interaction of PA peptide with neurons and with microglia, resulting in oxidative stress mediated cytotoxicity. Blocking RAGE with anti-RAGE F(αβ')$_2$ prevented the appearance of TNFβ messenger RNA and diminished TNFβ antigen to levels seen in untreated cells. Thus, it is postulated that RAGE mediates microglial activation by βA peptide by producing cytotoxic cytokines that cause neuronal damage in AD patients. In addition, RAGE was also demonstrated to specifically bind with βA peptide and mediate βA peptide-induced oxidative stress.

Cell receptors that bind to βA peptide have been identified. The low-affinity neurotrophin receptor p75 (p75NTR) which belongs to the family of apoptotic receptors that generate cell-death signals on activation was found throughout the brains of AD patients. βA peptide was found to be a ligand for p75NTR, and to cause preferential apoptosis of neurons and normal neural crest-derived melanocytes that express p75NTR upon specifically binding to p75NTR. See Zhang et al., *J Neurosci* 23, 7385 (2003) and Perini et al., *J Exp Med* 195, 907 (2002).

Basal forebrain cholinergic neurons express the highest levels of p75NTR in the adult human brain and have been shown to be involved in AD. The expression of p75NTR neuronal cells was shown to potentiate βA peptide-induced cell death. This interaction of βA peptide with p75NTR to mediate neuronal death in AD suggested a new target for therapeutic intervention. See Zhang et al., *J Neurosci* 23, 7385 (2003) and Perini et al., *J Exp Med* 195, 907 (2002).

Recently, ERAB which is over-expressed in neurons of the AD brain, was shown to bind with βA peptide to induce neuronal death in AD. Blocking ERAB with an antibody, anti-ERAB F(ab')$_2$, was found to reduce the βA peptide-induced cell death while ERAB overexpression increases βA peptide-induced cell death. See Frackowiak et al., *Brain Res* 907, 44 (2001) and Yan et al., *J Biol Chem* 274, 2145 (1999).

In designing inhibitors of βA peptide toxicity, it was found that neither the alteration of the apparent secondary structure of βA peptide nor the prevention of βA peptide aggregation is required to abrogate the cytotoxicity of βA peptide. Nonetheless, inducing changes in aggregation kinetics and in higher order structural characteristics of βA peptide aggregates also proved to be effective in reducing βA peptide toxicity. See Soto et al., *Neuroreport* 7, 721 (1996). Synthetic inhibitors that interact with βA peptide were shown to completely block βA peptide toxicity against PC12 cells, demonstrating that complete disruption of amyloid fibril formation is not necessary for abrogation of toxicity. It was also demonstrated that dipolar compounds such as phloretin and exifone that decrease the effective negative charge of membranes can prevent the association of βA peptide with negatively charged lipid vesicles and thereby prevent βA peptide-induced cytotoxicity. See Hertel et al., *Proc. Natl. Acad. Sci. USA* 94, 9412 (1997). These results suggest that PA peptide toxicity can be mediated through a physicochemical interaction with cell membranes.

Glaucoma and age-related macular degeneration (AMD) are the most common leading cause of irreversible progressive visual dysfunction that leads to blindness. Glaucoma causes irreversible vision loss worldwide an estimated 66.8 million people. See Khaw et al., *BMJ* 320, 1619 (2000). AMD is the leading cause of blindness and vision loss in developing countries due to increased life expectancy and subsequent increase in aged population. See VanNewkirk et al., *Ophthalmol* 108, 960 (2001). Between 20 and 25 million people are affected by AMD worldwide, a figure that will triple with the increase in the aging population in the next 30~40 years. See Smith et al., *Ophthalmol* 108, 697 (2001) and McCarty et al., *Arch Ophthalmol* 119, 1455 (2001). There are over 200,000 cases of neovascular degeneration that present to ophthalmologist in the United States each year. See Bressler et al., *BMJ* 321, 1425 (2000) and Chopdar et al., *BMJ* 326, 485 (2003). Glaucoma and AMD have profound effect on the family members and other loved ones who provide most of the care for people having this disease. Unfortunately, the cure for glaucoma and AMD has not yet been discovered.

AMD is characterized by abnormal extracellular deposits, known as drusen, the hallmark sign of AMD, that accumulate along the basal surface of the retinal pigmented epithelium. Although drusen is common in older individuals, large numbers of drusen and/or extensive areas of confluent drusen represent a significant risk factor for AMD. Widespread drusen deposition is associated with retinal pigmented epithelial cell dysfunction and degeneration of the photoreceptor cells. See Johnson et al., *Proc Natl Acad Sci USA* 99, 11830

(2002). There are two types of AMD, dry and wet. The dry type of AMD is characterized by a geographic atrophy that progresses slowly over many years. In the wet type of AMD choroidal neovascularization occurs that result in a dense fibrovascular scar that may involve the entire macular area. The wet type of AMD is more sight threatening than the dry type and is responsible for 90% of cases of severe visual loss in elderly population. See Chopdar et al., *BMJ* 326, 485 (2003).

Glaucoma is a chronic neurodegeneration of the optic nerve, retinal ganglion cells, that result in irreversible vision loss. See Khaw et al., *BMJ* 320, 1619 (2000).

The pathogenesis of glaucoma and AMD has recently been linked to deposition of beta-amyloid (βA) in retinal cells of the eyes. It was recently demonstrated that retinal ganglion cell death in glaucoma involves βA neurotoxicity at the molecular level. See McKinnon et al., *IOVS* 43, 1077 (2002). βA was also shown to associate with a substructural vesicular component within drusen and was found to correlate with the location of degenerating photoreceptors and retinal pigmented epithelium cells. See Dentchev et al., *Mol Vis* 14, 184 (2003). βA deposition was found an important component of the local inflammatory events that contribute to atrophy of the retinal pigmented epithelium, drusen biogenesis and the pathogenesis of AMD. See Johnson et al., *Proc Natl Acad Sci USA* 99, 11830 (2002).

Thus, therapeutic approaches that can modulate βA toxicity have been hypothesized to represent important methods for controlling the onset of glaucoma and macular degeneration. It is envisioned that if retinal cells can be protected from βA-induced toxicity, the onset of glaucoma and AMD may be delayed or prevented.

Current glaucoma treatment focuses on lowering intraocular pressure, the major risk factor for the disease. Glaucoma has been treated medically, surgically, or with laser to lower intraocular pressure that can slow the disease progression. Pharmacological treatment approaches are: cholinergic agents (pilocarpine—increases outflow of the aqueous humour; beta blockers—reduce aqueous secretion), oral carbonic anhydrase inhibitors (acetazolamide and dorzolamide—reduces aqueous secretion), alpha-2 adrenergic agonists (apraclonidine and brimonidine), and prostaglandin agonists (latanoprost—opens up an alternative pathway for aqueous outflow by altering the resistance of the extracellular matrix). See Khaw et al., *BMJ* 320, 1619 (2000) and Khaw et al., *BMJ* 328, 156 (2004).

One current treatment approach for AMD is a technique called photodynamic therapy that uses verteporfin as the photosensitizer. Long term supplementation with high dose zinc and antioxidant vitamins (A, C, and E) showed a significant reduction in the relative risk of developing neovascular AMD. As a preventive measure against the disease progression and the onset of AMD, carotenoids lutein and zeaxanthin, which are potent antioxidants found in high concentrations in the macular retina are found to be effective. See. Chopdar et al., *BMJ* 326, 485 (2003).

One important pharmacological approach related to βA-induced neurodegenerative disease preventive and neuroprotective interventions may be antioxidant therapy. See Kumar et al., *Int J Neurosci* 79, 185 (1994), Lucca, et al., *Brain Res* 764, 293 (1997), Manelli et al., *Brain Res Bull* 38, 569 (1995), Parnetti et al., *Drugs* 53, 752 (1997), Preston et al., *Neurosci Lett* 242, 105 (1998), and Zhou, et al., *J Neurochem* 67, 1419 (1996). In designing inhibitors of βA toxicity, it was found that inducing changes in aggregation kinetics and in higher order structural characteristics of βA aggregate may prove to be effective in reducing βA toxicity. See Ghanta et al., *J Biol Chem* 271, 29525 (1996). Synthetic inhibitors that interact with βA was shown to completely block βA toxicity against PC12 cells, demonstrating that complete disruption of amyloid fibril formation is not necessary for abrogation of toxicity. See Yaar et al., *J Clin Invest* 100, 2333 (1997) and Hertel et al., *Proc Natl Acad Sci USA* 94, 9412 (1997). These results suggest that βA toxicity can be mediated through a physicochemical interaction with cell membranes.

There is strong interest in discovering potentially valuable natural sources for drug development. One reasonable source of such natural products involves medicinal plants that have been in use throughout history for treating various ailments. Thus, the discovery of potentially valuable plants that can protect neurons from βA insult is of interest.

*Curcuma longa* (Zingiberaceae) has been used as curry spice and a well known constituent of Indonesian traditional medicine. See Nurfina et al., *Eur J Med Chem* 32, 321 (1997). One of the important constituents of turmeric is curcumin that has been known as a natural antioxidant with antitumor activity. See Ruby et al., *Cancer Lett* 94, 79 (1995). From turmeric, curcuminoids with antioxidant property have been demonstrated to protect neuronal cells from βA insult. See Kim DSHL et al., *Neurosci Lett* 303, 57 and Park S Y et al., *J Nat Prod* 65, 1227 (2002). A representative list of *Curcuma* sp. include *C. longa, C. aromatica, C. domestica, C. xanthorrhiza,* and *C. zedoaria.*

*Zingiber officinale* (Zingiberaceae) is one of the world's favorite spices, probably discovered in the tropics of Southeast Asia. Ginger has benefited humankind as a wonder drug since the beginning of recorded history. See Jitoe et al., *J Agric Food Chem* 40, 1337 (1992), Kikuzaki et al., *J Food Sci* 58, 1407 (1993) and Schulick, Herbal Free Press, Ltd. (1994). From ginger, shogaols with antioxidant property have also been demonstrated to protect neuronal cells from βA insult. See Kim et al., *Planta Medica* 68, 375 (2002). A representative list of *Zingiber* sp. include *Z. officinale, Z. zerumbet,* and *Z. mioga.*

*Ginkgo* (*Ginkgo biloba* (Ginkgoaceae)) is an herbal that has been used to treat neurologic ailment for thousand years as an Asian traditional medicine. *Ginkgo* leaf extract has shown to exhibit potent antioxidant activity and are widely used in the dietary supplement industry. The antioxidant activity of ginkgo has shown to be primarily contributed by diterpenes such as ginkgolides, bilobilide, flavonoids, and ginkgolic acids. See Hopia et al., *J Agric Food Chem* 44, 2030 (1996) and Nakatani et al., *Agric Biol Chem* 47, 353 (1983).

Sage (*Salvia officinalis* L. (Lamiaceae)) and Rosemary (*Rosmarinus officinalis* L. (Labiatae)) are spices widely used for flavoring and seasoning foods. These spices have shown to contain potent diterpenoid antioxidants such as carnosic acid, carnosol, rosmarinic acid, rosmanol, epirosmanol, rosmadial, isorosmanol etc. See Haraguchi et al., *Planta Med* 61, 333 (1995). Inatani et al, *Agric Biol Chem* 47: 521 (1983). Nakatani et al., *Agric Biol Chem* 48: 2081 (1984). Inatani et al., *Agric Biol Chem* 46: 1661 (1982). Wang et al., *J Agric Food Chem* 46: 2509 (1998). Wang et al., *J Agric Food Chem* 46: 4869 (1998).

SUMMARY OF THE INVENTION

The present invention relates to the identification and isolation of natural compounds present in turmeric, ginger, gingko biloba, sage, and rosemary that exhibit potent anti-βA peptide activity. The invention further provides novel synthetic compounds exhibiting potent anti-βA peptide activity which includes but is not limited to, the ability to neutralize amyloid protein mediated cytotoxicity towards retinal cells that relate to the pathogenesis of glaucoma and AMD. Specifically, the invention provides compounds and pharmaceutical compositions capable of protecting neurons from βA peptide insult, and methods for treating βA protein-induced disease with the same. In addition, it has been found that compounds derived from sage and rosemary and their analogs and homologs as described in co-owned and copending U.S. Provisional Patent Application Ser. No. 60/739,797 filed Nov. 23, 2005 entitled "Synergistic Pharmaceutical Compositions Useful in Prevention and Treatment of Beta-Amyloid Protein-Induced Disease Including Sage and Rosemary Derived Compounds" the disclosure of which is hereby incorporated by reference. These compounds have potent anti-Beta-amyloid activity alone and may be combined with the other turmeric, ginger, and ginkgo-biloba derived compounds and their analogs and homologues have anti Beta-amyloid activity to treat beta-Amyloid protein-induced ocular disease including age-related macular degeneration (AMD) and glaucoma.

As used herein, synthetic turmeric, ginger, *ginkgo biloba*, sage, or rosemary compounds include chemically synthesized versions of naturally occurring turmeric sp., ginger sp., *ginko biloba*, sage sp., or rosemary sp. compounds respectively as well as analogues and homologues of such naturally occurring compounds which have anti-βA peptide activity. As used herein anti-βA peptide activity includes, but is not limited to, the ability to neutralize amyloid protein mediated cytotoxicity including neurotoxicity.

Thus, the present invention is directed to treating (which when used herein also includes preventing) βA-involved ocular disease glaucoma and AMD. According to one aspect of the invention, an extract containing natural compounds found in turmeric (as well as synthetic analogues and homologues thereof) as the major ingredients or components and the natural compounds found in turmeric (as well as synthetic analogues and homologues thereof), may be administered to protect retinal cells from βA-involved cytotoxicity. Natural compounds that are suitable for use with the invention include, but are not limited to 4"-(3'"-methoxy-4'"-hydroxyphenyl)-2"-oxo-3"-enebutanyl 3-(3'-methoxy-4'-hydroxyphenyl)propenoate (calebin-A) and 1,7-bis(4-hydroxy-3-methoxyphenyl)-1,4,6-heptatrien-3-one, and seven known compounds, 1,7-bis(4-hydroxy-3-methoxyphenyl)-1,6-heptadiene-3,5-dione (curcumin), 1-(4-hydroxy-3-methoxyphenyl)-7-(4-hydroxyphenyl)-1,6-heptadiene-3,5-dione (demethoxycurcumin), 1,7-bis(4-hydroxyphenyl)-1,6-heptadiene-3,5-dione (bisdemethoxycurcumin), 1-hydroxy-1,7-bis(4-hydroxy-3-methoxyphenyl)-6-heptene-3,5-dione, 1,7-bis(4-hydroxyphenyl)-1-heptene-3,5-dione, 1,7-bis(4-hydroxyphenyl)-1,4,6-heptatrien-3-one, and 1,5-bis(4-hydroxy-3-methoxyphenyl)-1,4-pentadien-3-one,
2-shogaol, 4-shogaol, 6-shogaol, 8-shogaol, 10-shogaol, 12-shogaol, 2-gingerol, 4-gingerol, 6-gingerol, 8-gingerol, 10-gingerol, 12-gingerol, ginkgolic acids, rosmanol, isorosmanol, rosmadial, carnosol, carnosic acid, epirosmanol, rosmarinic acid etc.

In one aspect, the invention relates to a method for the treatment of a beta-Amyloid protein-induced disease including but not limited to Alzheimer's Disease (AD), age-related macular degeneration (AMD) and glaucoma comprising administering to a subject suffering from the beta-Amyloid protein-induced disease a therapeutically effective amount of a compound having the formula (I):

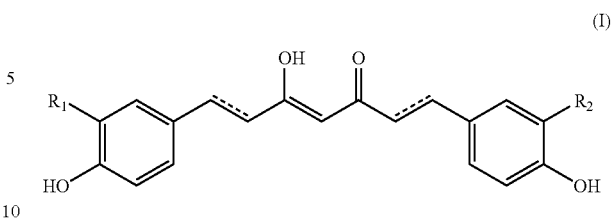

In this formula, the dotted configuration is optionally a single bond or a double bond. Generally, $R_1$ is selected from the group consisting of OH, OMe, $OR_{50}$, and X wherein $R_{50}$ is alkyl, alkenyl, or alkynyl, and X is F, Cl, Br, or I. Preferably, $R_1$ is selected from the group consisting of OH, OMe, $OR_{50}$ and X wherein $R_{50}$ is $(CH_2)_nCH_3$ and n is 1-7 and X is F, Cl, Br, or I. More preferably, $R_1$ is selected from the group consisting of H, OH, and OMe. Even more preferably, $R_1$ is OH. Even more preferably, $R_1$ is selected from the group consisting of H and OMe when the dotted configuration of compound (I) is a double bond, and $R_1$ is selected from the group consisting of H and OH when the dotted configuration is a single bond. Generally, $R_2$ is selected from the group consisting of OH, OMe, $OR_{50}$, and X wherein $R_{50}$ is alkyl, alkenyl, or alkynyl, and X is F, Cl, Br, or I. Preferably, $R_2$ is selected from the group consisting of OH, OMe, $OR_{50}$ and X wherein $R_{50}$ is $(CH_2)_nCH_3$ and n is 1-7 and X is F, Cl, Br, or I. More preferably, $R_2$ is selected from the group consisting of H, OH, and OMe. Even more preferably, $R_2$ is OH. Even more preferably, $R_2$ is selected from the group consisting of H and OMe when the dotted configuration of compound (I) is a double bond, and $R_2$ is H when the dotted configuration is a single bond.

Other compounds useful for practice of the invention include those of the formula (II):

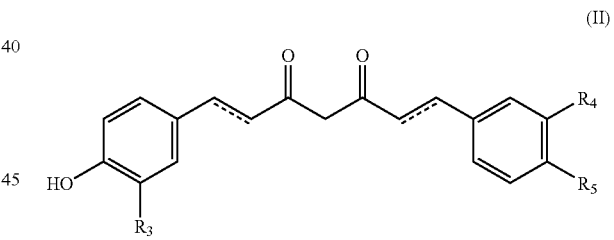

In this formula, the dotted configuration is optionally a single bond or a double bond or a triple bond. Generally, $R_3$ is selected from the group consisting of OH, OMe, $OR_{50}$, and X wherein $R_{50}$ is alkyl, alkenyl, or alkynyl, and X is F, Cl, Br, or I. Preferably, $R_3$ is selected from the group consisting of OH, OMe, $OR_{50}$ and X wherein $R_{50}$ is $(CH_2)_nCH_3$ and n is 1-7 and X is F, Cl, Br, or I. More preferably, $R_3$ is selected from the group consisting of H, OH, and OMe. Even more preferably, $R_3$ is H. Generally, $R_4$ is selected from the group consisting of OH, OMe, $OR_{50}$, and X wherein $R_{50}$ is alkyl, alkenyl, or alkynyl, and X is F, Cl, Br, or I. Preferably, $R_4$ is selected from the group consisting of OH, OMe, $OR_{50}$ and X wherein $R_{50}$ is $(CH_2)_nCH_3$ and n is 1-7 and X is F, Cl, Br, or I. More preferably, $R_4$ is selected from the group consisting of H, OH, and OMe. Even more preferably, $R_4$ is H. Even more preferably, $R_4$ is H when the first dotted configuration of compound (II) is a double bond and the second dotted configuration of compound (II) is a single bond, $R_4$ is H when both dotted configurations are single bonds, and $R_4$ is selected from the group consisting of H and OMe when both dotted configurations are double bonds. Generally, $R_5$ is selected from the group consisting of H, OH, OMe, $OR_{50}$, and X wherein $R_{50}$ is alkyl, alkenyl, or alkynyl, and X is F, Cl, Br, or I. Preferably, $R_5$ is selected from the group consisting of H, OH, OMe, $OR_{50}$, and X wherein $R_{50}$ is $(CH_2)_nCH_3$ and n is 1-7, ans X is F, Cl, Br, or I. More preferably, $R_5$ is selected from the group consisting of H, OH, and OMe. Even more preferably, $R_5$ is OH.

While compounds of formula (II) have been presented herein as diketones, and compounds of formula (I) have been presented as enols, those of skill in the art recognize that diketones and enols can coexist in solution as tautomers as shown below.

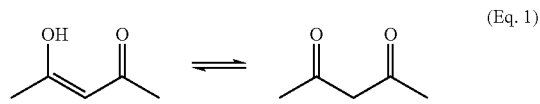

(Eq. 1)

Accordingly, the invention contemplates the use and production of compounds in either tautomeric form, and as a mixture of the two forms.

A natural product compound having the following general formula was isolated from turmeric, and was found to protect cells from βA peptide-induced toxicity.

Still other turmeric-related compounds useful in practice of the invention include those of formula (III):

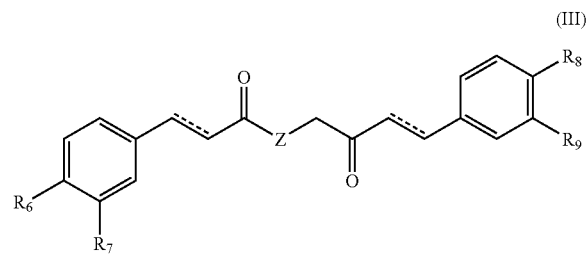

(III)

In this formula, the dotted configuration is optionally a single bond or a double bond or a triple bond. Z is a representation of isosteric variation in which Z is selected from O, S, NH, $NR_{60}$, where $R_{60}$ is alkyl, alkenyl, or alkynyl. Generally, $R_6$ is selected from the group consisting of OH, OMe, $OR_{50}$, and X wherein $R_{50}$ is alkyl, alkenyl, or alkynyl, and X is F, Cl, Br, or I. Preferably, $R_6$ is selected from the group consisting of OH, OMe, $OR_{50}$ and X wherein $R_{50}$ is $(CH_2)_nCH_3$ and n is 1-7 and X is F, Cl, Br, or I. More preferably, $R_6$ is selected from the group consisting of OH and OMe. Even more preferably, $R_6$ is OH. Generally, $R_7$ is selected from the group consisting of OH, OMe, $OR_{50}$, and X wherein $R_{50}$ is alkyl, alkenyl, or alkynyl, and X is F, Cl, Br, or I. Preferably, $R_7$ is selected from the group consisting of OH, OMe, $OR_{50}$ and X wherein $R_{50}$ is $(CH_2)_nCH_3$ and n is 1-7 and X is F, Cl, Br, or I. More preferably, $R_7$ is selected from the group consisting of H, OH, and OMe. Even more preferably, $R_7$ is H. Generally, $R_8$ is selected from the group consisting of OH, OMe, $OR_{50}$, and X wherein $R_{50}$ is alkyl, alkenyl, or alkynyl, and X is F, Cl, Br, or I. Preferably, $R_8$ is selected from the group consisting of OH, OMe, $OR_{50}$ and X wherein $R_{50}$ is $(CH_2)_nCH_3$ and n is 1-7 and X is F, Cl, Br, or I. More preferably, $R_8$ is selected from the group consisting of H, OH, and OMe. Even more preferably, $R_8$ is OH. Generally, $R_9$ is selected from the group consisting of OH, OMe, $OR_{50}$, and X wherein $R_{50}$ is alkyl, alkenyl, or alkynyl, and X is F, Cl, Br, or I. Preferably, $R_9$ is selected from the group consisting of OH, OMe, $OR_{50}$ and X wherein $R_{50}$ is $(CH_2)_nCH_3$ and n is 1-7 and X is F, Cl, Br, or I. More preferably, $R_9$ is selected from the group consisting of H, OH, and OMe. Even more preferably, $R_9$ is H.

The second set of compounds useful for practice of the invention include natural compounds which can be extracted on otherwise derived from *Ginkgo biloba* as well as synthetic *Ginkgo biloba* compounds including biologically active homologues and analogues of natural *Ginkgo biloba* compounds which share anti-βA activity. Such compounds have the formula (IV):

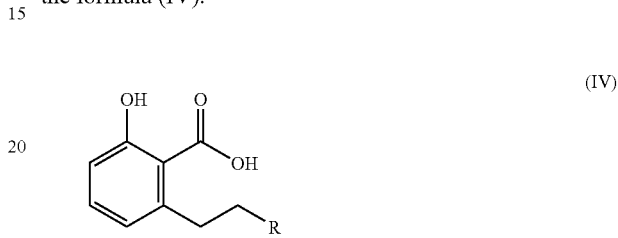

(IV)

or a pharmaceutically acceptable salt or ester thereof, wherein R is selected from the group consisting of higher alkyl, higher alkenyl, and higher alkynyl.

More preferably, R is

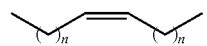

and n is 1-7. Even more preferably, R is selected from the group consisting of

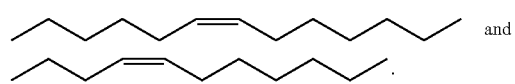

and

And R is also selected from the group consisting of alkyl, alkenyl, and alkynyl; for example;

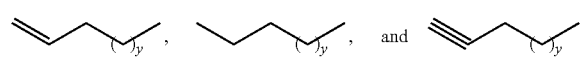

and y is 1-9, or having more than one double bond (cis or trans), or triple bond consisting of; for example;

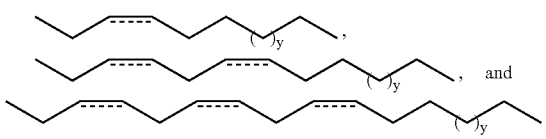

wherein the dotted line configuration is optionally a single bond (cis or trans), or a triple bond, wherein the alkyl, alkenyl, and alkynyl group is selected from ethers and/or thioethers or amines; for example;

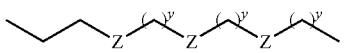

wherein Z=O, S, $NR_n$, where R=alkyl, alkenyl, alynyl groups; and n=1 or 2.

The third set of compounds useful for practice of the invention include natural compounds which can be extracted on otherwise derived from *Zingiber* sp. (ginger) as well as synthetic ginger compounds including biologically active homologues and analogues of natural ginger compounds which share anti-βA activity. Such compounds have the formula (V):

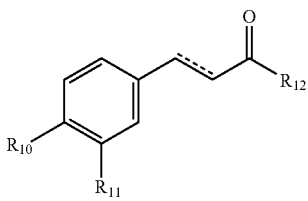

In this formula, the dotted configuration is optionally a single bond or a double bond or a triple bond. Preferably, $R_{10}$ is selected from the group consisting of OH, OMe, OR', and X wherein R' is alkyl, alkenyl, or alkynyl, and X is F, Cl, Br, or I. More preferably, $R_{10}$ is selected from the group consisting of OH, OMe, OR", and X wherein R" is $(CH_2)_nCH_3$ and n is 1-7, and X is F, Cl, Br, or I. Even more preferably, $R_{10}$ is OH. Preferably, $R_{11}$ is selected from the group consisting of H, OH, OMe, and OR' where R' is alkyl, alkenyl, or alkynyl. More preferably, $R_{11}$ is selected from the group consisting of H, OH, OMe, and OR" wherein R" is $(CH_2)_nCH_3$ and n is 1-7. Even more preferably, $R_{11}$ is selected from the group consisting of H and OMe. Preferably, $R_{12}$ is selected from the group consisting of alkyl, alkenyl, and alkynyl. More preferably, $R_{12}$ is selected from the group consisting of

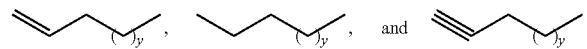

and y is 1-9. Even more preferably, $R_{12}$ is selected from the group consisting of

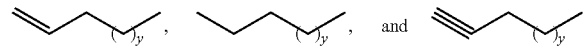

and y is 1-9, or having more than one double bond (cis or trans), or triple bond consisting of; for example;

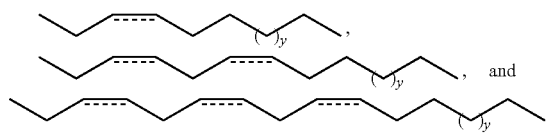

wherein the dotted line configuration is optionally a single bond (cis or trans), or a triple bond, wherein the alkyl, alkenyl, and alkynyl group is selected from ethers and/or thioethers or amines; for example;

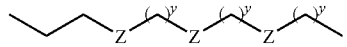

wherein Z=O, S, $NR_n$, where R=alkyl, alkenyl, alynyl groups; and n=1 or 2.

And compounds having a formula (VI):

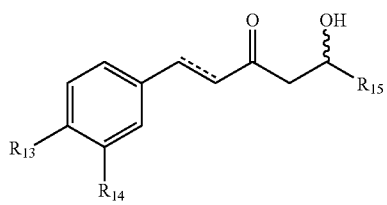

In this formula, the dotted configuration is optionally a single bond or a double bond or a triple bond. Preferably, $R_{13}$ is selected from the group consisting of OH, OMe, OR', and X wherein R' is alkyl, alkenyl, or alkynyl, and X is F, Cl, Br, or I. More preferably, $R_{13}$ is selected from the group consisting of OH, OMe, OR", and X wherein R" is $(CH_2)_nCH_3$ and n is 1-7, and X is F, Cl, Br, or I. Even more preferably, $R_{13}$ is OH. Preferably, $R_{14}$ is selected from the group consisting of H, OH, OMe, and OR' wher R' is alkyl, alkenyl, or alkynyl. More preferably, $R_{14}$ is selected from the group consisting of H, OH, OMe, and OR" wherein R" is $(CH_2)_nCH_3$ and n is 1-7. Even more preferably, $R_{14}$ is selected from the group consisting of H and OMe. Preferably, $R_{15}$ is selected from the group consisting of alkyl, alkenyl, and alkynyl. More preferably, $R_{15}$ is selected from the group consisting of

and y is 1-9. Even more preferably, $R_{15}$ is selected from the group consisting of

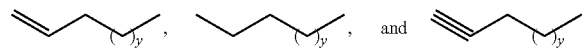

and y is 1-9, or having more than one double bond (cis or trans), or triple bond consisting of; for example;

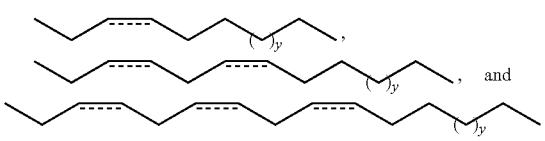

wherein the dotted line configuration is optionally a single bond (cis or trans), or a triple bond, wherein the alkyl, alkenyl, and alkynyl group is selected from ethers and/or thioethers or amines; for example;

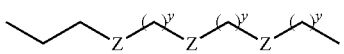

wherein Z=O, S, NR$_n$, where R=alkyl, alkenyl, alynyl groups; and n=1 or 2.

It is apparent from the biological results for the ginger-derived natural product compounds that the length of the side chain is important for the expression of biological activity. For example, with respect to the ginger-derived natural product compounds, compounds (11), (12), (13) and (14), the biological activity appears to improve as the compounds' side chain length increases. Thus, it is of interest to prepare analogues having different and lengthier side-chains. Preferably, shogaol compounds have side chains wherein R$_{12}$ has five or more carbons. More preferably, R$_{12}$ has nine or more carbons, and even more preferably, R$_{12}$ has eleven or more carbons. Furthermore, two of the synthesized shogaol analogue compounds, compounds (45) and (50), also effectively protected cells from βA peptide insult despite the fact that these compounds have different substituents than the ginger-derived natural product compounds. For example, compound (45) differs from the ginger-derived natural product compounds because it has a saturated hydrocarbon side chain, and compound (50) differs from the ginger-derived natural product compounds because it does not have a methoxy substituent. These data suggest that changing the nature of the substituents on the phenyl rings of the active compounds is of interest for the methods, pharmaceutical compositions, compounds and uses according to the invention.

As used herein, the term "alkyl" refers to a carbon chain having at least two carbons. Preferably, alkyl refers to a carbon chain having between two and twenty carbons. More preferably, alkyl refers to a carbon chain having between two and eight carbons. The term "alkenyl," as used herein, refers to a carbon chain having at least two carbons, and at least one carbon-carbon double bond. Preferably, alkenyl refers to a carbon chain having between two and twenty carbons, and at least one carbon-carbon double bond. More preferably, the term alkenyl refers to a carbon chain having between two and eight carbons, and at least one carbon-carbon double bond. The term "alkynyl," as used herein, refers to a carbon chain having at least two carbon atoms, and at least one carbon-carbon triple bond. Preferably, alkynyl refers to a carbon chain having between two and twenty carbon atoms, and at least one carbon-carbon triple bond. More preferably, alkynyl refers to a carbon chain having between two and eight carbon atoms, and at least one carbon-carbon triple bond.

As used herein, the term "higher alkyl" refers to a carbon chain having at least five carbon atoms. Preferably, higher alkyl refers to a carbon chain having between five and twenty carbons. More preferably, higher alkyl refers to a carbon chain having between five and twelve carbon atoms. As used herein, the term "higher alkenyl" refers to a carbon chain having at least five carbon atoms, and at least one cabon-carbon double bond. Preferably, higher alkenyl refers to a carbon chain having between five and twenty carbon atoms, and at least one carbon-carbon double bond. More preferably, higher alkenyl refers to a carbon chain having between five and twelve carbon atoms, and at least one carbon-carbon double bond. The term "higher alkynyl," as used herein, refers to a carbon chain having at least five carbon atoms, and at least one carbon-carbon triple bond. Preferably, higher alkynyl refers to a carbon chain having between five and twenty carbon atoms, and at least one carbon-carbon triple bond. More preferably, the term higher alkynyl refers to a carbon chain having between five and twelve carbon atoms, and at least one carbon-carbon triple bond.

The fourth set of compounds useful for practice of the invention include natural compounds which can be extracted or otherwise derived from *Salvia* sp. (sage) and *Rosmarinus* sp. (rosemary) which share anti-βA activity. Such compounds have the formulas (VII), (VIII), and (IX):

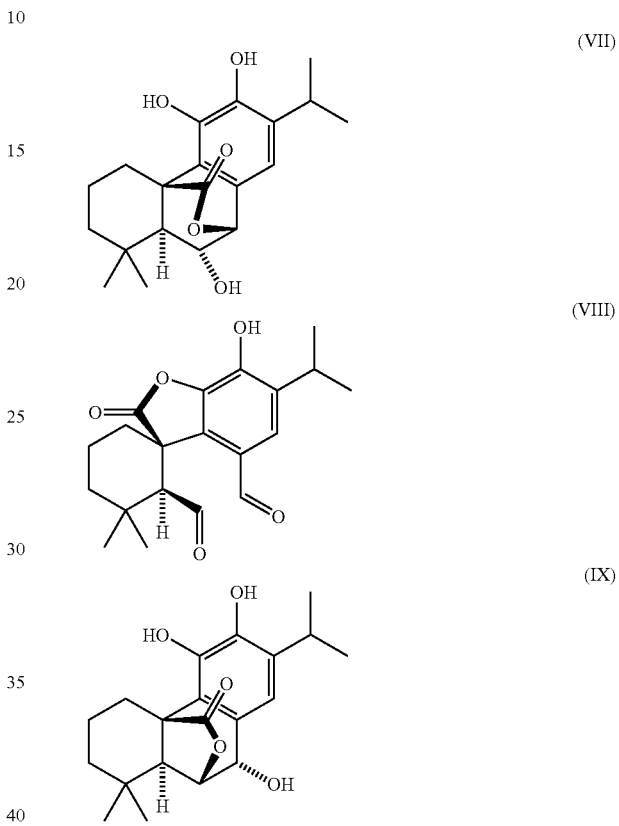

According to one aspect of the invention, combinations of each of the anti-Beta amyloid compounds may be administered as well as combinations of compounds of natural or synthetic compounds selected from the different classes of tumeric, *ginkgo biloba*, ginger, sage and rosemary compounds may be administered in combination for additive or synergistic effect. The invention also provides methods whereby the plant-derived compounds and homologues and analogues thereof may be combined with other agents including those selected from the group consisting of cholinergic agents (such as pilocarpine, beta blockers), oral carbonic anhydrase inhibitors (such as acetazolaminde and dorzolamide), alpha-2 adrenergic agonists (such as apraclonidine and brimonidine), prostaglandin agonists (latanoprost), carotenoids, lutein and zeaxanthin.

BRIEF DESCRIPTION OF THE DRAWINGS

These and other features, aspects, and advantages of the present invention will become better understood with regard to the following description, appended claims, and accompanying drawings where:

DETAILED DESCRIPTION OF THE INVENTION

Figure 1:
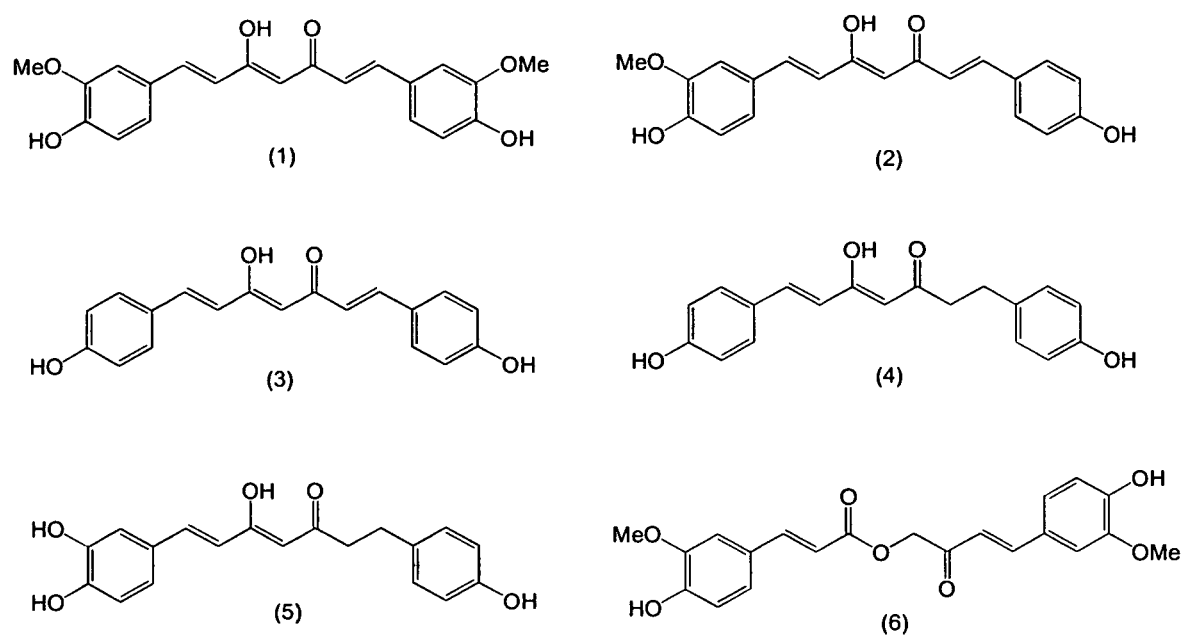
FIG. 1 shows the structures of turmeric-derived natural product compounds that protected PC12, IMR32, and HUVEC cells from βA peptide-induced toxicity.

One aspect of the present invention is directed to the use of methanol and other extract of *Curcuma* sp. (Zingiberaceae), *Zingiber* sp. (Zingiberaceae), *Ginkgo biloba, Salvia* sp. (Lamiaceae) and *Rosmarinus* sp. (Labiatae) to effectively protect cells from PA insult. The extract is obtained by pharmacologically acceptable solvent that is comprised of but not limited to methanol, ethanol, isopropyl alcohol, butanol etc. of such nature, and other nonalcoholic solvents such as dimethylsulfoxide, dimethyl formate, chloroform, dichloromethane, hexanes, petroleum ether and diethyl ether types, and in combination with water. The extracts of these plants were found to protect PC12, IMR32, and HUVEC cells from βA insult. Via bio-assay guided fractionation, twelve natural product compounds (eleven known and one novel) exhibiting potent anti-βA peptide activity were isolated and identified. These natural product compounds were found to protect PC12, IMR32, HUVEC, and primary cortical rat neuronal cells from βA peptide (both 25-35 and 1-42) insult.

In some cases, the natural product compounds were synthetically prepared. It is necessary and cost efficient to chemically synthesize the compounds in order to perform a thorough bioassay because only a small amount of these compounds are available from the natural sources. The biological activities of the synthesized natural product compounds were identical to those of the natural product compounds isolated from the plants. A series of natural product analogues that protect cells from βA peptide insult as effectively as the isolated natural product compounds were also synthesized.

Methods of treating a beta-Amyloid protein-induced ocular disease including AD, AMD and glaucoma with the compounds of the invention are described herein. Further, pharmaceutical compositions comprising one or more compounds of the invention and a pharmaceutically acceptable diluent, adjuvant, or carrier are provided. The use of the compounds of the invention for the manufacture of a medicament for treatment of a beta-amyloid protein-induced ocular disease is also disclosed herein.

Natural product compounds having the following general formula were isolated from turmeric and were found to protect cells from βA peptide insult. In addition, several of the natural product compounds described by this general formula were synthetically prepared.

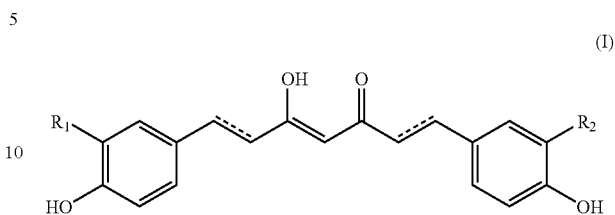

(I)

In this formula, the dotted configuration is optionally a single bond or a double bond. Generally, $R_1$ is selected from the group consisting of H, OH, OMe, and $OR_{50}$ wherein $R_{50}$ is alkyl, alkenyl, or alkynyl. Preferably, $R_1$ is selected from the group consisting of H, OH, OMe, and $OR_{60}$ wherein $R_{60}$ is $(CH_2)_nCH_3$ and n is 1-7. More preferably, $R_1$ is selected from the group consisting of H, OH, and OMe. Even more preferably, $R_1$ is selected from the group consisting of H and OMe when the dotted configuration of compound (I) is a double bond, and $R_1$ is selected from the group consisting of H and OH when the dotted configuration is a single bond. Generally, $R_2$ is selected from the group consisting of H, OMe, and $OR_{50}$ wherein $R_{50}$ is alkyl, alkenyl, or alkynyl. Preferably, $R_2$ is selected from the group consisting of H, OMe, and $OR_{60}$ wherein $R_{60}$ is $(CH_2)_nCH_3$ and n is 1-7. More preferably, $R_2$ is selected from the group consisting of H and OMe. Even more preferably, $R_2$ is selected from the group consisting of H and OMe when the dotted configuration of compound (I) is a double bond, and $R_2$ is H when the dotted configuration is a single bond.

Other compounds useful for practice of the invention include those of the formula (II):

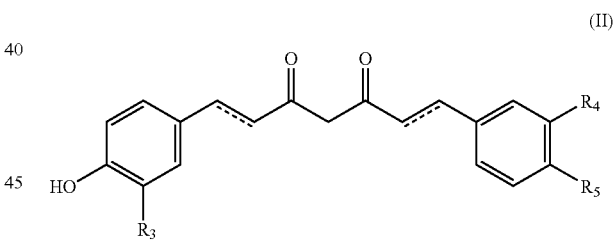

(II)

In this formula, the dotted configuration is optionally a single bond or a double bond or a triple bond. Generally, $R_3$ is selected from the group consisting of H, OMe, and $OR_{50}$ wherein $R_{50}$ is alkyl, alkenyl, or alkynyl. Preferably, $R_3$ is selected from the group consisting of H, OMe, and $OR_{60}$ wherein $R_{60}$ is $(CH_2)_nCH_3$ and n is 1-7. More preferably, $R_3$ is selected from the group consisting of H and OMe. Even more preferably, $R_3$ is H. Generally, $R_4$ is selected from the group consisting of H, OH, OMe, and $OR_{50}$ wherein $R_{50}$ is alkyl, alkenyl, or alkynyl. Preferably, $R_4$ is selected from the group consisting of H, OH, OMe, and $OR_{60}$ wherein $R_{60}$ is $(CH_2)_nCH_3$ and n is 1-7. More preferably, $R_4$ is selected from the group consisting of H, OH, and OMe. Even more preferably, $R_4$ is H when the first dotted configuration of compound (II) is a double bond and the second dotted configuration of compound (II) is a single bond, $R_4$ is H when both dotted configurations are single bonds, and $R_4$ is selected from the group consisting of H and OMe when both dotted configurations are double bonds. Generally, $R_5$ is selected from the group consisting of H, OH, OMe, $OR_{50}$, and X wherein $R_{50}$ is alkyl, alkenyl, or alkynyl, and X is F, Cl, Br, or I. Preferably, $R_5$ is selected from the group consisting of H, OH, OMe, $OR_{60}$, and X wherein $R_{60}$ is $(CH_2)_nC_3$ and n is 1-7, ans X is F, Cl, Br, or I. More preferably, $R_5$ is selected from the group consisting of H, OH, and OMe. Even more preferably, $R_5$ is OH.

While compounds of formula (II) have been presented herein as diketones, and compounds of formula (I) have been presented as enols, those of skill in the art recognize that diketones and enols can coexist in solution as tautomers as shown below.

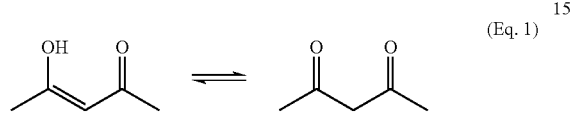

(Eq. 1)

Accordingly, the invention contemplates the use and production of compounds in either tautomeric form, and as a mixture of the two forms.

A natural product compound having the following general formula was isolated from turmeric, and was found to protect cells from βA peptide-induced toxicity.

Still other turmeric-related compounds useful in practice of the invention include those of formula (III):

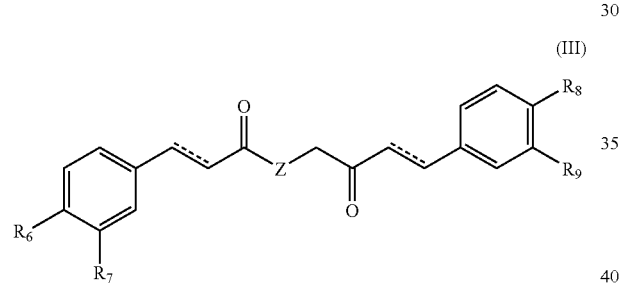

(III)

In this formula, the dotted configuration is optionally a single bond or a double bond or a triple bond. Z is a representation of isosteric variation in which Z is selected from O, S, NH, $NR_{60}$, where $R_{60}$ is alkyl, alkenyl, or alkynyl. Generally, $R_6$ is selected from the group consisting of OH, OMe, $OR_{50}$, and X wherein $R_{50}$ is alkyl, alkenyl, or alkynyl, and X is F, Cl, Br, or I. Preferably, $R_6$ is selected from the group consisting of OH, OMe, $OR_{60}$ and X wherein $R_{60}$ is $(CH_2)_nCH_3$ and n is 1-7 and X is F, Cl, Br, or I. More preferably, $R_6$ is selected from the group consisting of OH and OMe. Even more preferably, $R_6$ is OH. Generally, $R_7$ is selected from the group consisting of H, OMe, and $OR_{50}$ wherein $R_{50}$ is alkyl, alkenyl, or alkynyl. Preferably, $R_7$ is selected from the group consisting of H, OMe and $OR_{60}$ wherein $R_{60}$ is $(CH_2)_nCH_3$ and n is 1-7. More preferably, $R_7$ is selected from the group consisting of H and OMe. Even more preferably, $R_7$ is OMe. Generally, $R_8$ is selected from the group consisting of OH, OMe, $OR_{50}$ and X wherein $R_{50}$ is alkyl, alkenyl, or alkynyl, and X is F, Cl, Br, or I. Preferably, $R_8$ is selected from the group consisting of OH, OMe, $OR_{60}$ and X wherein $R_{60}$ is $(CH_2)_nCH_3$ and n is 1-7, and X is F, Cl, Br, or I. More Preferably, $R_8$ is selected from the group consisting of OH and OMe. Even more preferably, $R_8$ is OH. Generally, $R_9$ is selected from the group consisting of H, OMe and $OR_{50}$ wherein $R_{56}$ is alkyl, alkenyl, or alkynyl. Preferably, $R_9$ is selected from the group consisting of H, OMe and $OR_{60}$ wherein $R_{60}$ is $(CH_2)_nCH_3$ and n is 1-7. More preferably, $R_9$ is selected from the group consisting of H and OMe. Even more preferably, $R_9$ is OMe.

The second set of compounds useful for practice of the invention include natural compounds which can be extracted on otherwise derived from *Ginkgo biloba* as well as synthetic *Ginkgo biloba* compounds including biologically active homologues and analogues of natural *Ginkgo biloba* compounds which share anti-βA activity. Such compounds have the formula (IV):

(IV)

or a pharmaceutically acceptable salt or ester thereof, wherein R is selected from the group consisting of higher alkyl, higher alkenyl, and higher alkynyl.

More preferably, R is

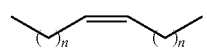

and n is 1-7. Even more preferably, R is selected from the group consisting of

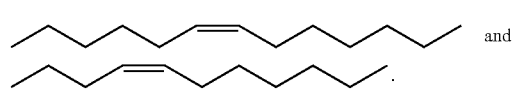

and

And R is also selected from the group consisting of alkyl, alkenyl, and alkynyl; for example;

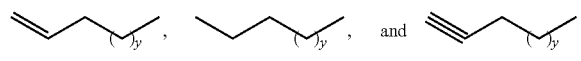

and y is 1-9, or having more than one double bond (cis or trans), or triple bond consisting of; for example;

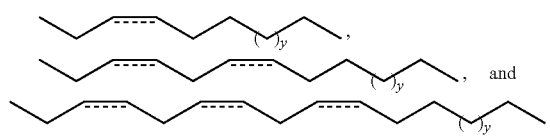

wherein the dotted line configuration is optionally a single bond (cis or trans), or a triple bond, wherein the alkyl, alkenyl, and alkynyl group is selected from ethers and/or thioethers or amines; for example;

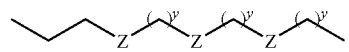

wherein Z=O, S, $NR_n$, where R=alkyl, alkenyl, alynyl groups; and n=1 or 2.

The third set of compounds useful for practice of the invention include natural compounds which can be extracted on otherwise derived from *Zingiber* sp. (ginger) as well as synthetic ginger compounds including biologically active homologues and analogues of natural ginger compounds which share anti-βA activity. Such compounds have the formula (V):

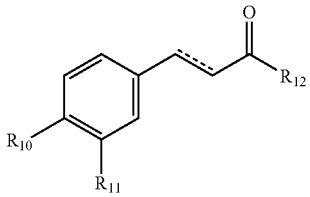

In this formula, the dotted configuration is optionally a single bond or a double bond or a triple bond. Preferably, $R_{10}$ is selected from the group consisting of OH, OMe, OR', and X wherein R' is alkyl, alkenyl, or alkynyl, and X is F, Cl, Br, or I. More preferably, $R_{10}$ is selected from the group consisting of OH, OMe, OR", and X wherein R" is $(CH_2)_nCH_3$ and n is 1-7, and X is F, Cl, Br, or I. Even more preferably, $R_{10}$ is OH. Preferably, $R_{11}$ is selected from the group consisting of H, OH, OMe, and OR' wher R' is alkyl, alkenyl, or alkynyl. More preferably, $R_{11}$ is selected from the group consisting of H, OH, OMe, and OR" wherein R" is $(CH_2)_nCH_3$ and n is 1-7. Even more preferably, $R_{11}$ is selected from the group consisting of H and OMe. Preferably, $R_{12}$ is selected from the group consisting of alkyl, alkenyl, and alkynyl. More preferably, $R_{12}$ is selected from the group consisting of
and y is 1-9.

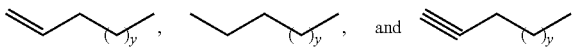

Even more preferably, $R_{12}$ is selected from the group consisting of

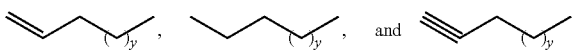

and y is 1-9, or having more than one double bond (cis or trans), or triple bond consisting of; for example;

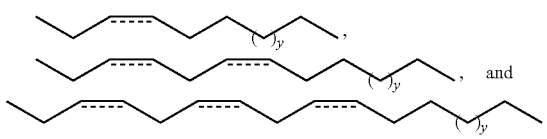

wherein the dotted line configuration is optionally a single bond (cis or trans), or a triple bond, wherein the alkyl, alkenyl, and alkynyl group is selected from ethers and/or thioethers or amines; for example;

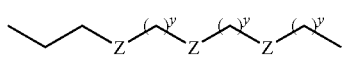

wherein Z=O, S, $NR_n$, where R=alkyl, alkenyl, alynyl groups; and n=1 or 2.

and y is 1-9.

And compounds having a formula (VI):

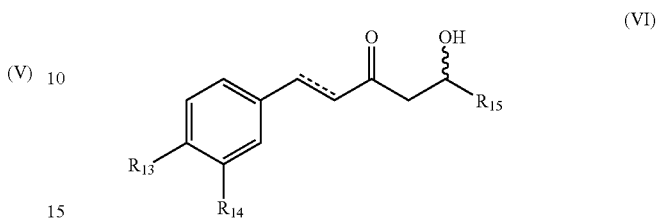

In this formula, the dotted configuration is optionally a single bond or a double bond or a triple bond. Preferably, $R_{13}$ is selected from the group consisting of OH, OMe, OR', and X wherein R' is alkyl, alkenyl, or alkynyl, and X is F, Cl, Br, or I. More preferably, $R_{13}$ is selected from the group consisting of OH, OMe, OR", and X wherein R" is $(CH_2)_nCH_3$ and n is 1-7, and X is F, Cl, Br, or I. Even more preferably, $R_{13}$ is OH. Preferably, $R_{14}$ is selected from the group consisting of H, OH, OMe, and OR' wher R' is alkyl, alkenyl, or alkynyl. More preferably, $R_{14}$ is selected from the group consisting of H, OH, OMe, and OR" wherein R" is $(CH_2)_nCH_3$ and n is 1-7. Even more preferably, $R_{14}$ is selected from the group consisting of H and OMe. Preferably, $R_{15}$ is selected from the group consisting of alkyl, alkenyl, and alkynyl. More preferably, $R_{15}$ is selected from the group consisting of

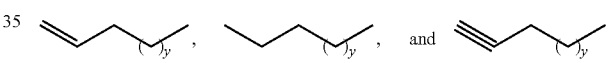

and y is 1-9, or having more than one double bond (cis or trans), or triple bond consisting of; for example;

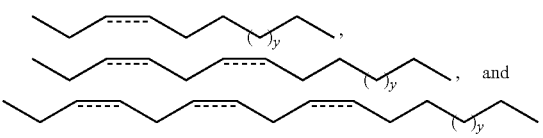

wherein the dotted line configuration is optionally a single bond (cis or trans), or a triple bond, wherein the alkyl, alkenyl, and alkynyl group is selected from ethers and/or thioethers or amines; for example;

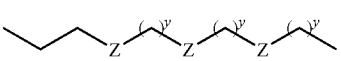

wherein Z=O, S, $NR_n$, where R=alkyl, alkenyl, alynyl groups; and n=1 or 2.

It is apparent from the biological results for the ginger-derived natural product compounds that the length of the side chain is important for the expression of biological activity. For example, with respect to the ginger-derived natural product compounds, compounds (11), (12), (13) and (14), the biological activity appears to improve as the compounds' side chain length increases. Thus, it is of interest to prepare analogues having different and lengthier side-chains. Preferably, shogaol compounds have side chains wherein $R_{12}$ has five or more carbons. More preferably, $R_{12}$ has nine or more carbons, and even more preferably, $R_{12}$ has eleven or more carbons. Furthermore, two of the synthesized shogaol analogue compounds, compounds (45) and (50), also effectively protected cells from βA peptide insult despite the fact that these compounds have different substituents than the ginger-derived natural product compounds. For example, compound (45) differs from the ginger-derived natural product compounds because it has a saturated hydrocarbon side chain, and compound (50) differs from the ginger-derived natural product compounds because it does not have a methoxy substituent. These data suggest that changing the nature of the substituents on the phenyl rings of the active compounds is of interest for the methods, pharmaceutical compositions, compounds and uses according to the invention.

As used herein, the term "alkyl" refers to a carbon chain having at least two carbons. Preferably, alkyl refers to a carbon chain having between two and twenty carbons. More preferably, alkyl refers to a carbon chain having between two and eight carbons. The term "alkenyl," as used herein, refers to a carbon chain having at least two carbons, and at least one carbon-carbon double bond. Preferably, alkenyl refers to a carbon chain having between two and twenty carbons, and at least one carbon-carbon double bond. More preferably, the term alkenyl refers to a carbon chain having between two and eight carbons, and at least one carbon-carbon double bond. The term "alkynyl," as used herein, refers to a carbon chain having at least two carbon atoms, and at least one carbon-carbon triple bond. Preferably, alkynyl refers to a carbon chain having between two and twenty carbon atoms, and at least one carbon-carbon triple bond. More preferably, alkynyl refers to a carbon chain having between two and eight carbon atoms, and at least one carbon-carbon triple bond.

As used herein, the term "higher alkyl" refers to a carbon chain having at least five carbon atoms. Preferably, higher alkyl refers to a carbon chain having between five and twenty carbons. More preferably, higher alkyl refers to a carbon chain having between five and twelve carbon atoms. As used herein, the term "higher alkenyl" refers to a carbon chain having at least five carbon atoms, and at least one cabon-carbon double bond. Preferably, higher alkenyl refers to a carbon chain having between five and twenty carbon atoms, and at least one carbon-carbon double bond. More preferably, higher alkenyl refers to a carbon chain having between five and twelve carbon atoms, and at least one carbon-carbon double bond. The term "higher alkynyl," as used herein, refers to a carbon chain having at least five carbons, and at least one carbon-carbon triple bond. Preferably, higher alkynyl refers to a carbon chain having between five and twenty carbon atoms, and at least one carbon-carbon triple bond. More preferably, the term higher alkynyl refers to a carbon chain having between five and twelve carbon atoms, and at least one carbon-carbon triple bond.

The fourth set of compounds useful for practice of the invention include natural compounds which can be extracted or otherwise derived from *Salvia* sp. (sage) and *Rosmarinus* sp. (rosemary) which share anti-βA activity. Such compounds have the formulas (VII), (VIII) and (IX):

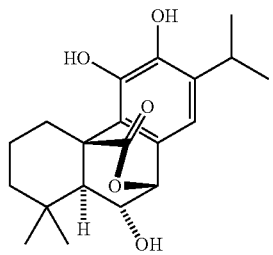
(VII)

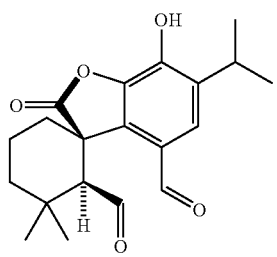
(VIII)

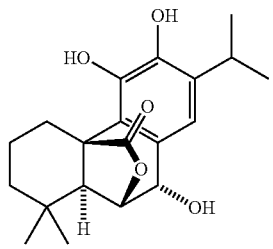
(IX)

The administration of the natural product and natural product analogue compounds of the invention is preferably accomplished with a pharmaceutical composition comprising a therapeutically effective amount of an active compound of the present invention and a pharmaceutically acceptable diluent, adjuvant, or carrier. A compound according to the invention may be administered without or in conjunction with known antibiotics, surfactants, or other therapeutic agents. It is contemplated that the pharmaceutical compositions of this invention can be administered to humans and other animals orally, rectally, parentally, intracisternally, intraperitoneally, intraocularly by injection or depot, topically (as by powders, ointments, or drops), intraocularly, bucally, intranasally, or by any other effective route of administration.

According to the methods for treatment of the present invention, βA protein-induced disease is treated in a subject, such as a human or lower mammal, by administering to the subject a therapeutically effective amount of an active compound of the invention in such amounts and for such time as is necessary to achieve the desired results. The term "beta-Amyloid protein-induced disease", as used herein, refers to disease states that are characterized by the formation and aggregation of beta-Amyloid protein or beta-Amyloid peptide fibril deposits or plaques, such as, for example, Alzheimer's disease, Down's syndrome, age-related macular degeneration (AMD) and glaucoma.

It is contemplated that the methods for treatment in accordance with the invention encompass the treatment of subjects wherein the βA protein-induced disease process is ongoing but wherein the subjects do not exhibit manifest outward symptoms, and/or wherein the pathology of the disease can not be detected using presently available technologies. Furthermore, the methods for treatment of the present invention contemplate not only treating the common symptoms associated with βA protein-induced diseases but also treating the pathology of the disease. Thus, the methods for treatment provided herein include treating symptoms associated with βA protein-induced diseases, such as, for example, the memory loss and dementia associated with Alzheimer's disease, but also include preventing senile plaque formations, and/or clearing such formations. Similarly, the methods of the invention are contemplated to be useful in treating the symptoms associated with βA-induced ocular diseases such as glaucoma and AMD and further treat the pathology of those diseases. It is hypothesized that the formation of senile plaques is a regularly occurring and ongoing process in humans and other mammals. However, it is further hypothesized that the equilibrium of this process is substantially disturbed in patients affected by βA protein-induced diseases, resulting in the accumulation and formation of senile and ocular plaques.

As used herein, the term "therapeutically effective amount" means that amounts of a compound of the present invention sufficient to alleviate, ameliorate, prevent, and/or clear the symptoms and/or the pathology of βA protein-induced disease are contemplated for administration. Accordingly, the methods for treatment of AD in accordance with the invention contemplate administration of an active compound of the invention whether βA protein-induced disease-like symptoms are manifest, or not.

The total daily dose of natural product compound (6) of this invention to be administered to a human or other mammal is preferably between 1 to 200 mg/kg body weight. More preferably, the total daily dosage is between 20 to 160 mg/kg body weight. Even more preferably, the total daily dosage is between 40 to 100 mg/kg body weight. One skilled in the art could obtain preferred dosage ranges for the other compounds of the invention by extrapolating from the compounds' $ED_{50}$ values, such as, for example the $ED_{50}$ values presented in Tables 1, 2, 3, and 4. It will be understood that the total daily usage of the compounds and compositions of the present invention will be decided by the attending physician within the scope of sound medical judgment. The specific therapeutically effective dose level for any particular patient will depend upon a variety of factors including the severity and progression of the disease, the time of administration, the route of administration, the size of the subject, the rate of excretion of the specific compound employed, the duration of the treatment, the additional therapeutic agents used in combination with the specific compound of the invention, and like factors well known in the medical arts.

The mechanism of action of the natural product compounds and the natural product analogue compounds of the invention appears to involve both antioxidant and non-antioxidant pathways. Without intending to be bound by a theory of the mechanism of the invention, it is believed that the compounds and compositions of the invention provide therapeutic and preventive agents that protect neurons from βA peptide insult by (1) an antioxidant pathway, (2) preventing the aggregation of βA peptide by directly binding to PA peptide, thereby altering its structural conformation and rendering it non-toxic, and/or (3) binding to a receptor site on the cell, thereby altering the cell function in such a way that it is protected from βA peptide toxicity.

The invention can be better understood in light of the following examples which are intended as an illustration of the practice of the invention and are not meant to limit the scope of the invention in any way.

EXAMPLE 1

Isolation and Identification of Natural Product Compounds Derived from Turmeric that Protect Cells from Beta Amyloid-Induced Toxicity According to this example, potent anti-AD natural product compounds that protect cells from βA peptide-induced toxicity were isolated from turmeric by following bioassay-guided fractionation schemes. Briefly, ground turmeric was extracted with 90% methanol overnight (2×), and the solvent was removed under vacuum at 35° C. The residue was partitioned between petroleum ether/water, dichloromethane/water, and ethyl acetate/water, successively. After removing the solvents under vacuum at 35° C., the residues from each partition were screened for inhibitory activity against βA peptide-induced cytotoxicity using the MTT assay described in this example. The active principles were isolated from the residues of the active fractions by a series of column chromatography using various resins (Amberchrom non-ionic resin and silica gel) and semi-preparative HPLC reverse-phased separation (isopropyl alcohol/water or acetonitrile/water solvent system). Six curcuminoids, natural product compounds (1), (2), (3), (4), (5), and (6) were isolated from turmeric, and their structures were elucidated using NMR (1-D and 2-D $^1$H, $^{13}$C, APT, HMBC) and mass spectrum analysis. These compounds are shown in FIG. 1.

The inhibitory activity of the residues and of the identified compounds was determined by observing the differences in the cell viability of βA peptide (both 25-35 and 1-42) treated cells, βA peptide (both 25-35 and 1-42) treated cells further including a compound according to the invention, and a DMSO control.

The degree of βA insult was measured by 3-[4,5-dimethylthiazol-2-yl]-2,5-diphenyltetrazolium bromide (MTT) reduction assay. See Kim et al., *Neurosci Lett* 303, 57 (2001), Park et al., *J Nat Prod* 65, 1227 (2002) and Kim et al., *Plant Medica* 68, 375 (2002). The detection of cell growth or cell death can be determined by observing the conversion of MTT to the colored product, MTT formazan, the concentration of which can be measured calorimetrically at 550 nm. See Kim et al., *Neurosci Lett* 303,57 (2001).

The βA peptide-induced toxicity inhibitory effects of the compounds were tested on PC12 cells. The cells were incubated with βA peptide (25-35) (1.0 µg/ml, made from 1.0 mg/ml stock solution in DMSO) or βA peptide (1-42) (2.0 µg/ml, made from 1.0 mg/ml stock solution in DMSO) and the test compounds at various concentrations (25, 5.0, 1.0, and 0.2 µg/ml) in collagen-coated 96-well tissue culture plates for 24 hours. The PA peptide-induced toxicity inhibitory effect of the compounds was determined by calorimetrically and microscopically evaluating the PC12 cells' potential to reduce MTT against a positive control (1% DMSO only) and a negative control (1.0 µg/ml βA peptide in 1% DMSO alone). Cells were incubated in MTT solution (5 mg/ml) at 37° C. for 2 hours. During this time, cells were observed under a microscope every 15 min. Cells were incubated in Lysing buffer (100 µl) overnight at 37° C. Colorimetric determination of MTT reduction was made at 550 nm. The βA peptide-induced cytotoxicity inhibitory activity of the compounds was also evaluated against IMR32, HUVEC, and primary cortical rat neuronal cells.

PC12 rat pheochromocytoma and IMR32 human neuroblastoma cells were obtained from the American Type Culture Collection (ATCC). HUVEC normal umbilical human vein endothelial cells were obtained from Clonetics (San Diego, Calif.). Cells were routinely cultured on a tissue culture plate (Corning, N.Y., N.Y.). PC12 cells were grown in high glucose Dulbecco's Modified Eagle Medium (DMEM), 10% horse serum, 5% fetal calf serum, and 1% penicillin/streptomycin. IMR32 cells were grown in 90% DMEM and 10% fetal calf serum with 1% penicillin/streptomycin. HUVEC cells were grown in EGM-2 Bullet Kit (Clonetics, San Diego, Calif.). For the bioassay using βA peptide(25-35) and βA peptide(1-42), 100 μl of exponentially growing PC12 cells (2,000 cells per ml) were plated in collagen-coated 96-well tissue culture plates.

PC12 cells were cultured routinely on polystyrene-coated Corning tissue culture plates. PC12 cells gave consistent results only when the collagen-coated 96-well plates were used. The 96-well plates were coated with rat tail collagen (Boehringer Mannheim) in order to promote uniform PC12 cell attachment and growth. Under the experimental conditions, βA peptide (25-35) and βA peptide (1-42) was toxic to PC12 cells at $ED_{50}=1.0$ and 5.0 μg/ml, respectively.

IMR32 and HUVEC cells were chosen to confirm and supplement the anti-PA peptide activity of the compounds identified by the assay using PC12 cells. βA peptide has been reported to be cytotoxic to IMR32 and endothelial cells. Experimental results demonstrated that IMR32 and HUVEC cells are sensitive to βA peptide (25-35) at $ED_{50}=3.0$ and 6.0 μg/ml, respectively, and βA peptide (1-42) at $ED_{50}=6.0$ and 10.0 μg/ml, respectively.

Primary cortical rat neuronal cells were obtained in the following manner. Dissociated primary neuronal cell cultures were established from 18-day-old Sprague-Dawley rat fetuses. The pups were delivered by caesarean section while the dam was anesthetized with ether. Hippocampal tissue from embryonic day 18 Sprague-Dawley rat pups was dissected and then rinsed in cold $Ca^{2+}/Mg^{2+}$-free Hank's balanced salt solution supplemented with 20 mM HEPES, 4.2 mM sodium bicarbonate, 1 mM pyruvate, and 3 mg/ml bovine serum albumin (BSA). Following gentle trituration of the tissue with a constricted pipette in cold buffer, two volumes of 10% fetal bovine serum (FBS) in DMEM were added to the suspension. After the suspension settled for 2 minutes, the supernatant was collected and centrifuged for 2 min. at 200×g. The cell pellets were resuspended in serum-free DMEM (pH 7.3), supplemented with 2.4 mg/ml BSA and a modification of Brewer's B16 defined components (with 250 nM vitamin B12 and without catalase, glutathione, and superoxide dismutase). Cells were plated at a density of 15,000 cells/cm² and grown at 37° C. After 24 hours of incubation to allow cell attachment, the serum-containing medium was replaced by defined medium with DMEM/F12 containing bovine transferrin (100 μg/ml), bovine insulin (5 μg/ml), putrescine (0.1 mM), progesterone (10 nM), sodium selenite (30 nM), sodium pyruvate (1 mM), and potassium bicarbonate (15 mM). Cells maintained for extended periods of time were fed twice a week by replacing ⅓ of the medium with fresh medium.

EXAMPLE 2

Inhibitory Activity and Antioxidant Potency of Turmeric-Derived Natural Product Compounds Against Beta Amyloid Toxicity According to this example, the inhibitory activity of the turmeric-derived natural product compounds (1), (2), (3), (4), (5), and (6) (shown in FIG. 1) against βA peptide-induced toxicity was measured by the MTT reduction assay described in example 1. These six turmeric-derived curcuminoids protected PC12, IMR32, and HUVEC cells from βA peptide-induced toxicity (Table 1). These compounds also protected primary cortical neuronal cells at 5 μg/ml against βA peptide (1-42) insult (10 μg/ml).

$ED_{50}$ values reflect the results from the MTT assay, and represent the sample concentration that is required to achieve 50% cell viability, a mid-point between the positive control values and the negative control values. The samples that gave values as determined by the MTT assay less than or equal to that of βA peptide treated wells were considered cytotoxic or without desired activity, and are labeled "toxic".

The measurement of lactate dehydrogenase activity released to the extracellular bathing media was also used to assess cell viability in cell culture. LDH activity in the medium was measured. See Kimura et al., *Brain Res* 1047, 72 (2005) and Loudina et al., *Exp Neurol* 184, 923 (2003). This assay was used to confirm the $ED_{50}$ results obtained in the MTT assay. Samples of media from 96-well cell culture plates were transferred to an empty well of a 96-well plate (100 μl) and 2.0 μmol of sodium pyruvate and 0.1 mg of the reduced form of nicotinamide adenine dinucleotide (NADH in 0.1 M $K_2PO_4$ buffer (pH 7.5 at 25° C.) were added (total volume of 400 μl). The absorbance of the reaction mixture at 340 nm provides an index of NADH concentration, and was recorded using a spectrophotometer 5 minutes after mixing the reagents. The experiment was performed in triplicate and the LDH concentration was calculated from the slope of the absorbance curve, fit by linear regression to the linear (initial) portion of the curve. The concentration of LDH was expressed in conventional units (u) per ml. Accuracy of the assay was verified by periodic checks of a standard LDH enzyme solution (Sigma).

$IC_{50}$ values reflect the results of the antioxidant assay described in this example, and represent the sample concentration which is required to scavenge 50% of the DPPH free radicals. Kim et al., *Neurosci Lett* 303, 57 (2001) and Barik et al., *Free Radic Biol Med* 39, 811 (2005).

Using an antioxidant assay, the antioxidant potency of the compounds of the invention was evaluated. 1,1-Diphenyl-2-picrylhydrazyl (DPPH) is known to generate stable free radicals in aqueous and ethanolic solutions. The ability of the compounds of the invention to scavenge these free radicals was measured by observing the optical density change of DPPH radicals at 515 nm. Kim et al., *Neurosci Lett* 303, 57 (2001) and Barik et al., *Free Radic Biol Med* 39, 811 (2005).

The samples were prepared in various concentrations (200, 20, 2.0, and 0.2 μg/ml) by serial dilution of a stock solution (5 mg/ml) and were tested by the following procedure. Reaction mixtures containing test compounds (dissolved in DMSO) and 300 μM DPPH ethanolic solution in 96-well microtiter plates were incubated at 37° C. for 30 min. and absorbance was measured at 515 nm. Percent inhibition by sample treatment was determined by comparison with a DMSO-treated positive control group. $IC_{50}$ values were determined from percent inhibition by sample. $IC_{50}$ values denote the concentration of the tested compound that was required to scavenge 50% of the DPPH free radicals.

The antioxidant potency of the natural product compounds was evaluated by measuring the compounds' ability to scavenge free radicals in order to elucidate the possible involvement of antioxidant pathways in the compounds ability to protect the cells (Tables 1 and 2). The results showed that only compounds (1) and (2) have strong antioxidant activity, suggesting that the compounds of the invention may be protecting cells from βA peptide insults through a mechanism that does not involve an antioxidant pathway.

TABLE 1

Inhibitory Activity of Turmeric-Derived Natural Product Compounds against βA Peptide-Induced Toxicity against PC12, IMR32, and HUVEC cells and Antioxidant Activity of the Compounds.

| Compound | Anti-βA peptide(25-35) $ED_{50}$ (µg/ml) PC12 | Anti-βA peptide(1-42) $ED_{50}$ (µg/ml) PC12 | Anti-βA peptide(25-35) $ED_{50}$ (µg/ml) IMR32 | Anti-βA peptide(25-35) $ED_{50}$ (µg/ml) HUVEC | Anti-βA peptide(1-42) $ED_{50}$ (µg/ml) HUVEC | Antioxidant $IC_{50}$ (µg/ml) |
|---|---|---|---|---|---|---|
| 1 | 7.0 | 10 | 6.0 | 12 | 13 | 28.2 |
| 2 | 4.0 | 5.0 | 4.0 | 4.5 | 5.0 | 36.2 |
| 3 | 2.0 | 3.5 | 2.5 | 2.4 | 2.0 | >200 |
| 4 | 0.5 | 1.0 | 1.2 | 0.8 | 1.0 | >200 |
| 5 | 2.5 | 3.0 | 1.5 | 2.0 | 1.5 | >200 |
| 6 | 1.0 | 2.0 | 1.0 | 1.5 | 1.0 | >200 |

EXAMPLE 3

Curcuminoid Analogue Synthesis

According to this example, curcuminoids and curcuminoid analogues were synthesized.

Figure 2:
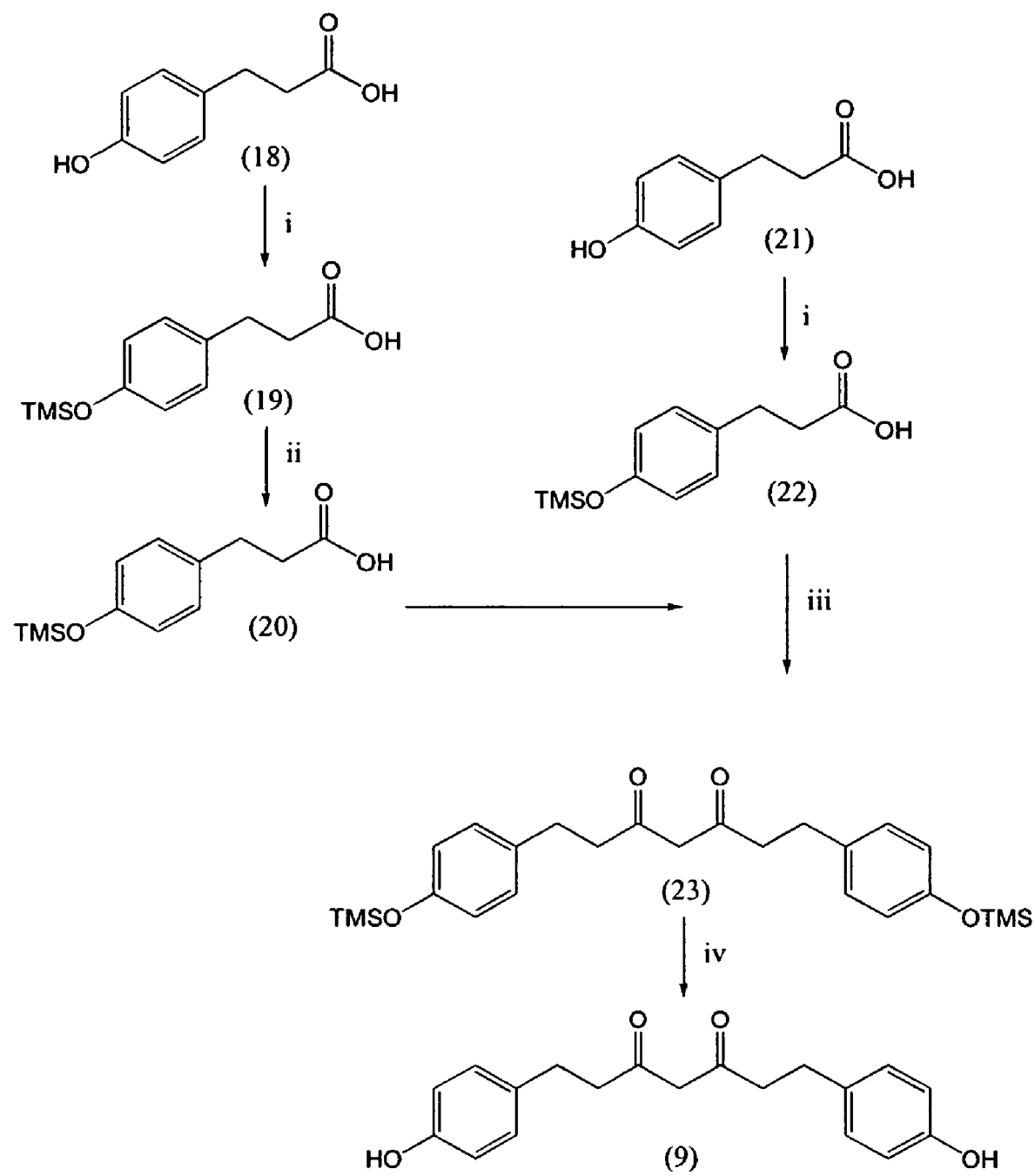
FIG. 2 shows a scheme for the synthesis of dihydro- and tetrahydro-curcuminoids.

Dihydro- and tetrahydro-curcuminoids were synthesized by the procedure illustrated in FIG. 2. 3-(4-hydroxyphenyl) propanoic acid, compound (18), was treated with TMSCl (1.3 equivalents) in the presence of 1.1 equivalents of triethylamine in THF/CH$_2$Cl$_2$ (50/50) solution to precipitate triethylammonium chloride as a white solid. The reaction was over within a few minutes, and only the phenolic position was protected. The white ammonium salt was filtered, and the filtrate was diluted with ethyl acetate. The resulting solution was washed with water three times, dried (MgSO$_4$), filtered, and the solvent was removed under vacuum to afford the TMS protected carboxylic acid, compound (19), in quantitative yield. The TMS protected carboxylic acid, compound (19), was converted to the corresponding acyl chloride, compound (20), by refluxing in oxalyl chloride for 30 min, and the remaining oxalyl chloride was removed under a stream of N$_2$ gas. 4-(4-hydroxyphenyl)-2-butanone, compound (21), was treated with TMSCl (1.3 equivalents) in the presence of triethylamine (1.1 equiv) in CH$_2$Cl$_2$, yielding the TMS protected product, compound (22). The ammonium chloride precipitate was filtered, and the filtrate was diluted with ethyl acetate. The resulting solution was washed with water (3×), dried (MgSO$_4$), filtered, and the solvent was removed under vacuum to afford compound (22), in quantitative yield. Compound (22) was treated with lithium diisopropylamide (LDA, 1.5 M in THF, 1. equiv) in tetrahydrofuran (THF) at −78° C. under N$_2$ for 20 min and 1.1 equivalents of the TMS protected acyl chloride, compound (20), dissolved in THF was added. The reaction mixture was stirred at −78° C. for 15 minutes and slowly warmed to room temperature. The reaction mixture was quenched with water and poured into ethyl acetate. The organic layer was washed three times with water and the water layer was back washed (2×) with ethyl acetate. The organic layers were combined, dried (MgSO$_4$), filtered, and the solvent was removed under vacuum. The residue was stirred in methanol in the presence of K$_2$CO$_3$ for 30 min to remove TMS protection. The solution was acidified with 2N HCl and poured into ethyl acetate. The aqueous layer was partitioned three times with ethyl acetate and the organic layers were combined, dried (MgSO$_4$), filtered, and the solvent was removed under vacuum. The residue was column chromatographed over silica gel using a gradient elution of ethyl acetate/petroleum ether to afford compound (9). Compound (9) was further purified using semi-preparative HPLC using an acetonitrile/water (90/10) solvent system to give pure synthesized curcuminoid compound (9) in 45% overall yield. Similarly, the unsymmetric synthesized curcuminoid compound (4) was prepared in 40% overall yield.

Figure 3:
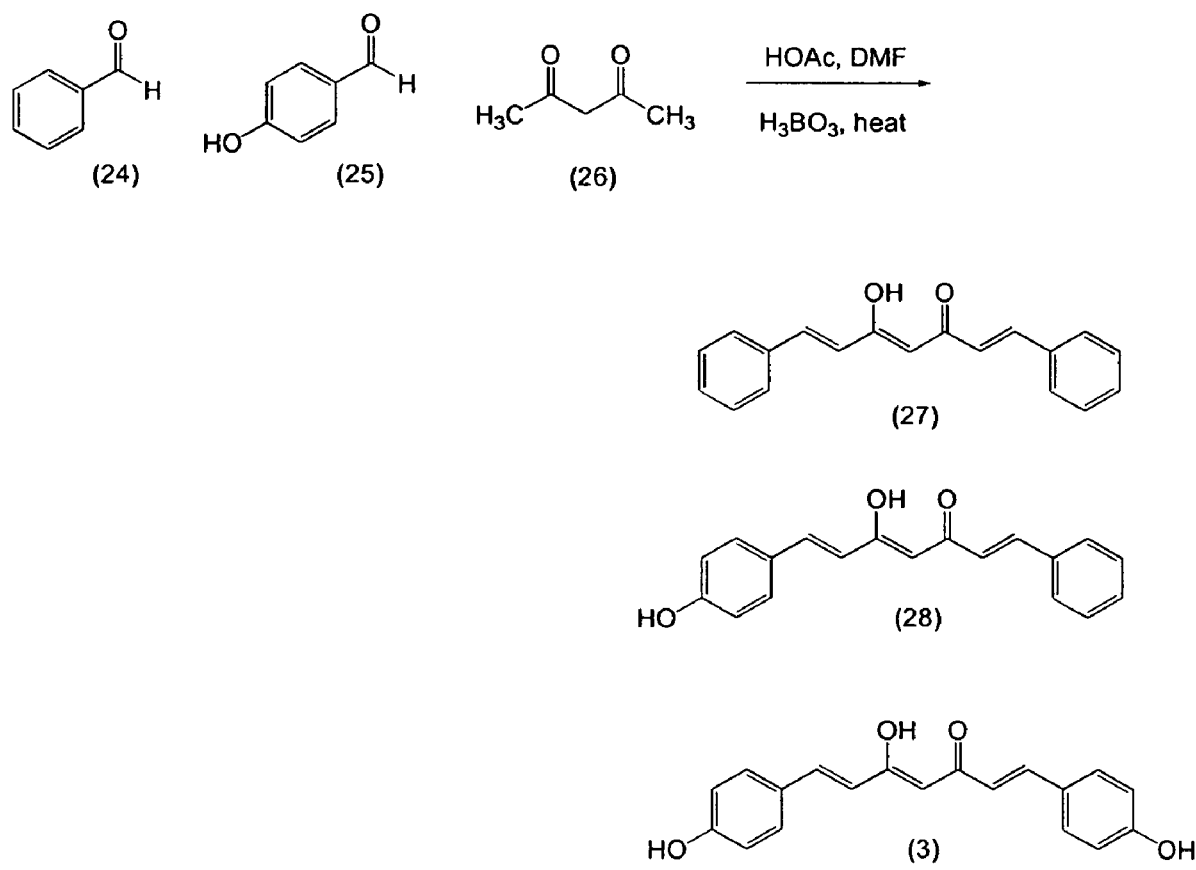
FIG. 3 shows a scheme for the synthesis of symmetric and unsymmetric curcumin analogues and related compounds.

Both symmetric and unsymmetric curcumin analogues and related compounds were prepared according to the procedure described in FIG. 3. Benzaldehyde, compound (24), 4-hydroxybenzaldehyde, compound (25), 2,4-pentadione, compound (26), and boric acid were dissolved in dry N,N-dimethylformamide (DMF), and treated with a small amount of 1,2,3,4-tetrahydroquinoline and glacial acetic acid. This reaction yielded three products: a diphenyl group substituted product, compound (27), in 31% yield, a dihydroxyphenyl group substituted product, compound (3), in 6% yield, and a hydroxyphenyl phenyl substituted product, compound (28), in 11% yield. After working up the reaction, (ethyl acetate/water partitioning and back washing of the aqueous layer with ethyl acetate, followed by drying (MgSO$_4$) of the organic layer and removal of solvent in vacuo), the products were separated using semi-preparative HPLC (75% isopropyl alcohol/H$_2$O eluent system). The physical data ($^1$H NMR) of the dihydroxyphenyl product (3) was identical to that of the turmeric-derived natural product (3).

Figure 4:
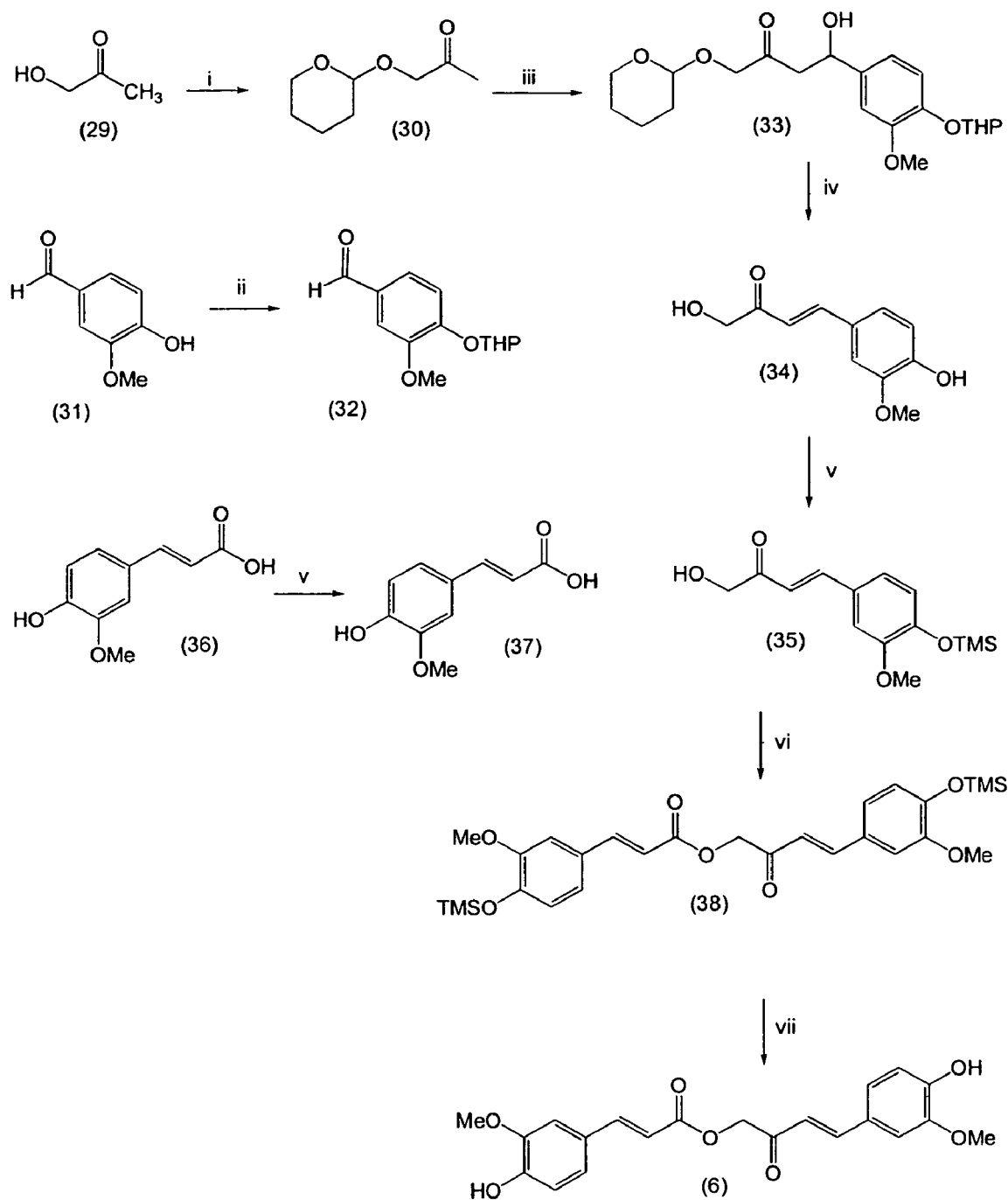
FIG. 4 shows a scheme for the synthesis of turmeric-derived natural product compound (6).

Natural product compound (6) was synthetically prepared according to the procedure shown in FIG. 4. The alcohol functionalities of acetol, compound (29), and vanillin, compound (31), were protected in quantitative yield as tetrahydropyran (THP) ethers using dihydropyran (DHP) in the presence of pyridinium para-toluene sulfonate (PPTS) in THF. The THP ether of acetol, compound (30), was reacted with LDA in THF at −78° C. and then reacted with the THP ether of vanillin, compound (32), to afford the β-hydroxy ketone, compound (33), in 73% yield. The THP ether was removed in the presence of PPTS, causing the dehydration of the β-hydroxyl group, and affording compound (34) in 72% yield. The phenolic group of compound (34) was selectively protected with a TMS group in quantitative yield to yield an alcohol, compound (35). The phenolic group of 4-hydroxy-3-methoxyphenyl propenoic acid, compound (36), was selectively protected with a TMS group in quantitative yield. The TMS protected carboxylic acid, compound (37), and the alcohol, compound (35), were coupled in the presence of dicyclohexylcarbodiimide (DCC) and dimethylamino-pyridine (DMAP) in THF at room temperature to afford 68% of the coupled product, compound (38). The TMS protecting groups of compound (38) were removed by stirring in a mixture of acetic acid/$H_2O$ in THF (1/1/5) to afford the desired product in 53% yield. Attempts to remove the TMS groups of compound (38) using tetra-n-butylammonium fluoride in THF resulted in the decomposition of the desired reaction product. The $^1$H NMR of the product was identical to that of turmeric-derived natural product compound (6).

EXAMPLE 4

Figure 5:
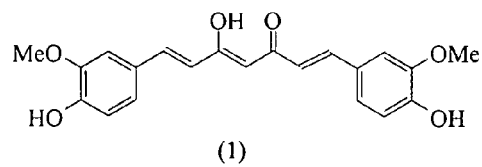
FIG. 5 shows the structures of curcuminoid compounds that have been synthetically prepared and assayed for biological activity against βA peptide-induced toxicity.
Figure 5:
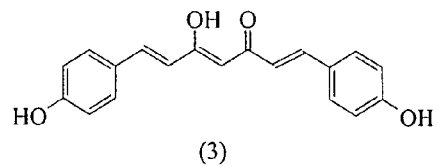
Figure 5:
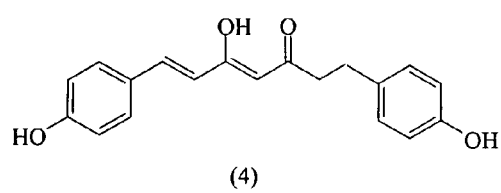
Figure 5:
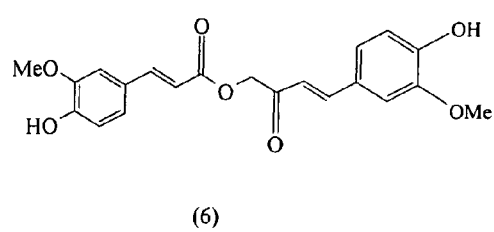
Figure 5:
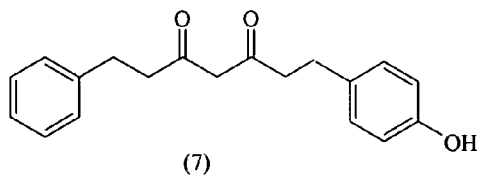
Figure 5:
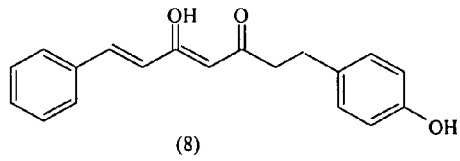
Figure 5:
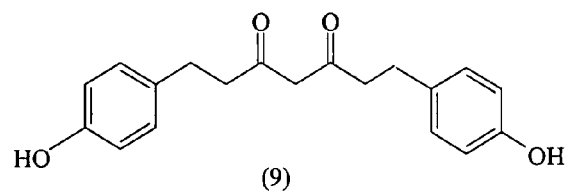
Figure 5:
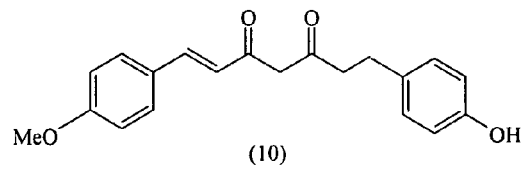
Figure 5:
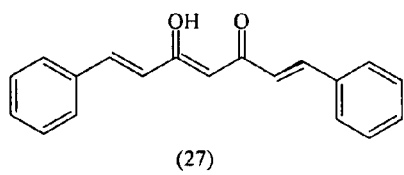
Figure 5:
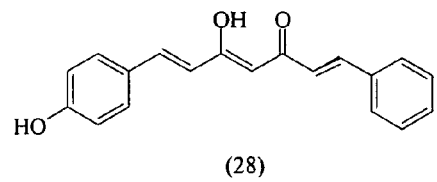

Inhibitory Activity and Antioxidant Potency of Curcuminoid Synthetic Analogues Against Beta Amyloid-Induced Toxicity According to this example, the inhibitory activity of the synthetic curcuminoid analogues against βA peptide-induced toxicity was measured by the MTT reduction assay described in example 1. Synthesized compounds (1), (3), (4), and (9) (shown in FIG. 5) protected the cells from βA peptide insult (Table 2). Microscopic analyses of βA peptide treated cells further including synthesized curcuminoid compounds (3) and (4) also demonstrated that these compounds effectively protect cells from βA peptide insults. The positive control and cells treated with compounds (3) and (4) maintained MTT formazan granules in the cytosole, a sign of viable cells, while the negative control showed extensive MTT formazan spike processes, a sign of nonviable cells. As was the case with the structurally analogous natural product compound, natural product compound (4), synthesized curcuminoid compound (4) provided the best protection. Interestingly, synthesized curcuminoid compounds (7), (8), and (10) were cytotoxic. Apparently, the presence of a hydroxyl group at the 4-position of phenyl ring or the size of substituent at that position is important for the expression of the desired biological activity. The results of the MTT assay were confirmed by the LDH methodology set forth in example 2. The synthesized curcuminoid compounds are shown in FIG. 5.

The ability of the synthesized curcuminoid compounds to scavenge DPPH free radicals was measured by observing the optical density change of the radicals at 515 nm in accordance with the antioxidant assay set forth in Example 2. The results show that only compounds 1 and 3 have significant antioxidant activity (Table 2).

EXAMPLE 5

Figure 6:
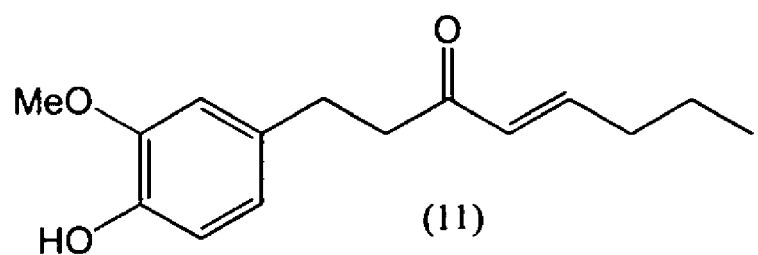
FIG. 6 shows the structures of ginger-derived natural product compounds that protected PC12, IMR32, and HUVEC cells from βA peptide-induced toxicity.
Figure 6:
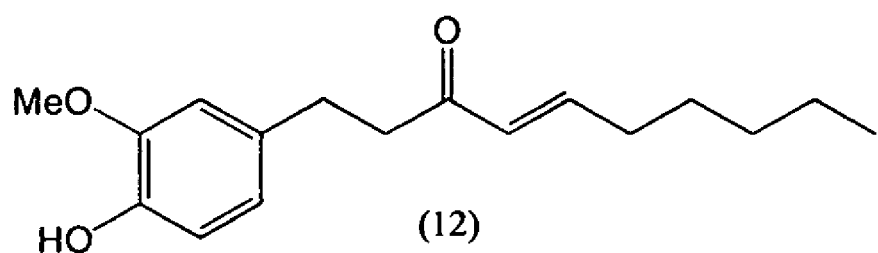
Figure 6:
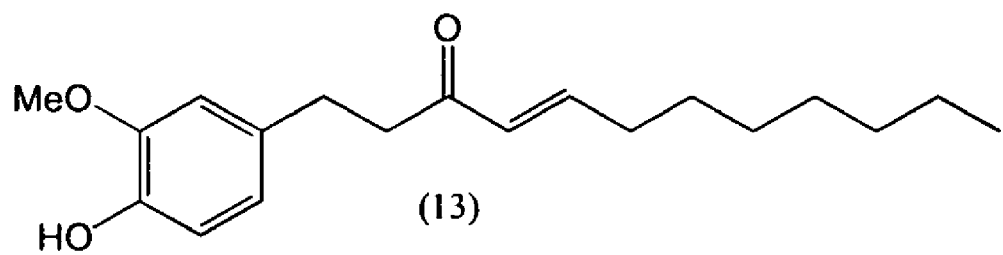
Figure 6:
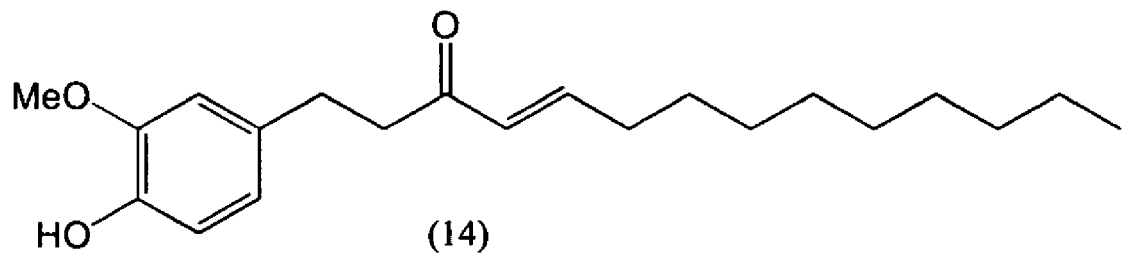

Isolation and Identification of Natural Product Compounds Derived from Ginger that Protect Cells from Beta Amyloid-Induced Toxicity According to this example, natural product compounds that protect cells from βA peptide-induced toxicity were isolated from ginger by following bioassay-guided fractionation schemes. Briefly, ground ginger was extracted with 90% methanol overnight (2×), and the solvent was removed under vacuum at 35° C. The residue was partitioned between petroleum ether/water, dichloromethane/water, and ethyl acetate/water, successively. After removing the solvent under vacuum at 35° C., the residues from each partition were screened for inhibitory activity against βA peptide-induced cytotoxicity using PC12, IMR32, and HUVEC cells at 25, 5.0, and 1.0 βg/ml. The active principles were isolated from the residues of active fractions by a series of column chromatography using various resins (Amberchrom non-ionic resin and silica gel) and semi-preparative HPLC reverse-phased separation (isopropyl alcohol/water or acetonitrile/water solvent system). Four shogaols, natural product compounds (11), (12), (13), and (14) (shown in FIG. 6) were isolated from ginger, and their structures were elucidated using NMR (1-D and 2-D $^1$H, $^{13}$C, APT, HMBC) and mass spectrum analysis.

EXAMPLE 6

Inhibitory Activity of Ginger-Derived Natural Product Compounds Against Beta Amyloid Toxicity According to this example, the inhibitory activity of natural product compounds (11), (12), (13), and (14) (shown in FIG. 6) against βA peptide-induced toxicity was measured by the MTT reduction assay set forth in example 1. These natural product compounds effectively protected PC12, IMR32, and HUVEC cells from βA peptide-induced toxicity (Table 2). The results of the MTT assay were confirmed by the LDH methodology set forth in example 2.

The ability of natural product compounds (11), (12), (13), and (14) to scavenge DPPH free radicals was measured by observing the optical density change of the radicals at 515 nm in accordance with the antioxidant assay set forth in Example 2. None of these compounds exhibited significant antioxidant activity.

TABLE 2

Inhibitory Activity of Synthesized Curcuminoids against βA Peptide-Induced Toxicity against PC12 and IMR32 Cells and Antioxidant Activity of the Compounds.

| Compound | Anti-βA peptide(25-35) $ED_{50}$ (μg/ml) PC12 | Anti-βA peptide(1-42) $ED_{50}$ (μg/ml) PC12 | Anti-βA peptide(25-35) $ED_{50}$ (μg/ml) IMR32 | Anti-βA peptide(1-42) $ED_{50}$ (μg/ml) IMR32 | Antioxidant $IC_{50}$ (μg/ml) |
|---|---|---|---|---|---|
| 1 | 5.5 | 6.0 | 6.0 | 6.0 | 28.5 |
| 3 | 3.0 | 4.5 | 3.0 | 3.5 | 32.6 |
| 4 | 0.5 | 1.0 | 1.5 | 2.0 | >200 |
| 7 | toxic | toxic | toxic | toxic | >200 |
| 8 | toxic | toxic | toxic | toxic | >200 |
| 9 | 10.0 | 9.0 | 12.0 | 11.0 | >200 |
| 10 | toxic | toxic | toxic | toxic | >200 |

TABLE 3

Inhibitory Activity of Ginger-Derived Natural Product Compounds against βA Peptide-Induced Toxicity against PC12, IMR32, and HUVEC cells and Antioxidant Activity of the Compounds.

| Compound | Anti-βA peptide(25-35) $ED_{50}$ (μg/ml) PC12 | Anti-βA peptide(1-42) $ED_{50}$ (μg/ml) PC12 | Anti-βA peptide(25-35) $ED_{50}$ (μg/ml) IMR32 | Anti-βA peptide(25-35) $ED_{50}$ (μg/ml) HUVEC | Anti-βA peptide(1-42) $ED_{50}$ (μg/ml) HUVEC | Antioxidant $IC_{50}$ (βg/ml) |
|---|---|---|---|---|---|---|
| 11 | 15 | 12 | 15 | 20 | 20 | >200 |
| 12 | 9.0 | 10 | 8.0 | 20 | 18 | >200 |
| 13 | 3.0 | 4.0 | 2.0 | 8.0 | 8.0 | >200 |
| 14 | 2.0 | 2.0 | 1.5 | 4.0 | 5.0 | >200 |

EXAMPLE 7

Shogaol Analogue Synthesis

According to this example, shogaols and their analogues were successfully synthesized in 100 mg scale. Gingerols were synthesized from zingerone by conversion into the corresponding O-trimethylsilyl ether, deprotonation with lithium bis(trimethylsilyl)amide or lithium diisopropylamide (LDA), and regioselective aldol condensation. Shogaols are gingerol analogues with a 4,5-double bond, resulting from the elimination of the 5-hydroxy group.

Figure 7:
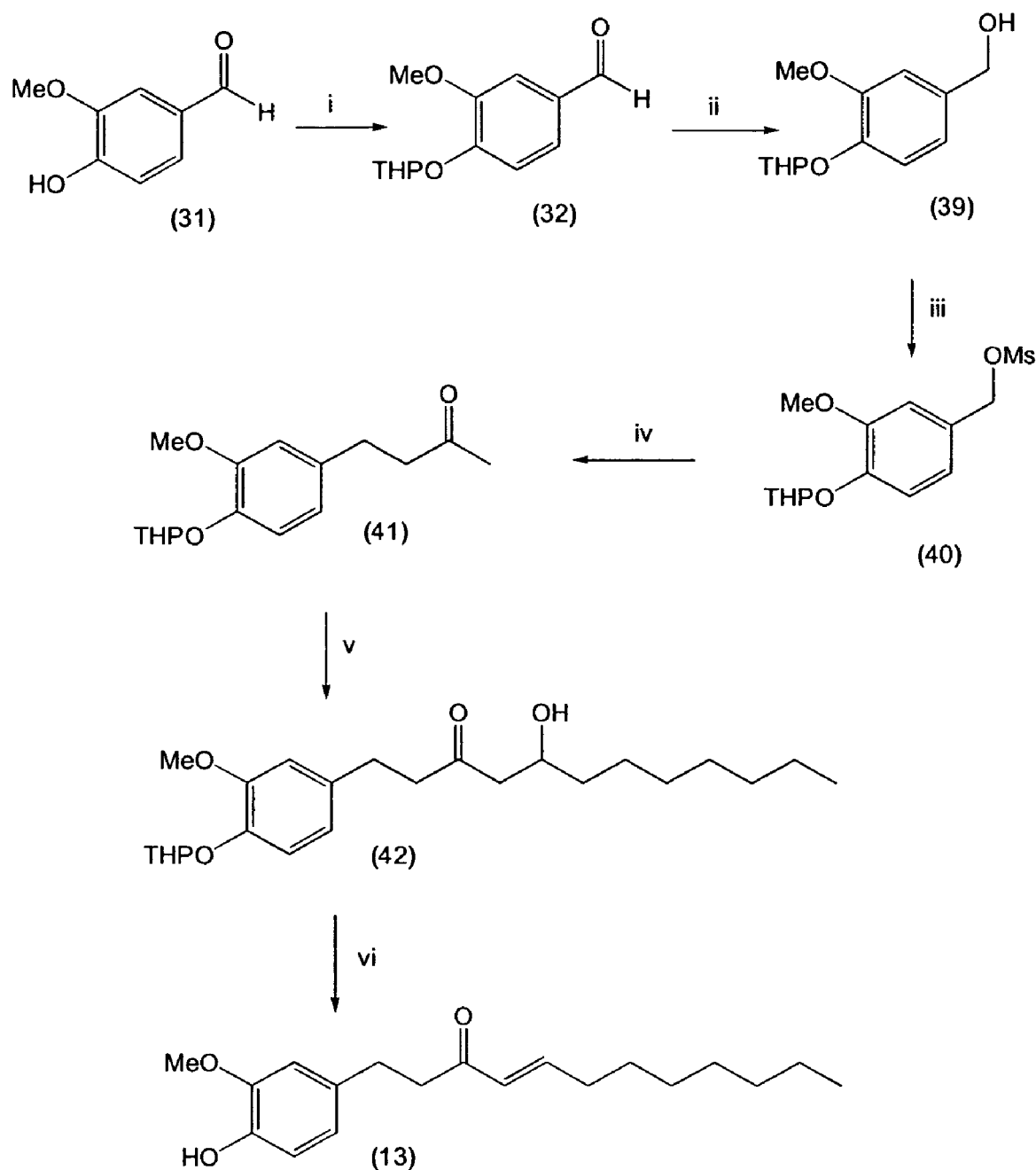
FIG. 7 shows a scheme for the synthesis of ginger-derived natural product compound (13).

The phenol group of vaniline, compound (31), was protected as the THP ether (DHP/PPTS/CH$_2$Cl$_2$) to yield compound (32), and the aldehyde group of compound (32) was reduced to the alcohol to yield compound (39) using NaBH$_4$ in THF as shown in FIG. 7. The resulting alcohol, compound (39), was mesylated (methanesulfonyl chloride/triethylamine/THF) and then reacted with in situ generated lithium acetonide (acetone/LDA/THF/−78° C.) at −78° C. under N$_2$ to yield compound (41). Compound (41) was reacted with LDA at −78° C. in THF under N$_2$ to generate lithium enolate which was then reacted with octyl aldehyde to afford the β-hydroxy ketone, compound (42). During treatment with PPTS in ethanol at 50° C. to remove the THP ether protecting group, dehydration occurred to afford [9]-shogaol, compound (13), which was identical to the ginger-derived natural product compound (13) (overall yield 37%).

Figure 8:
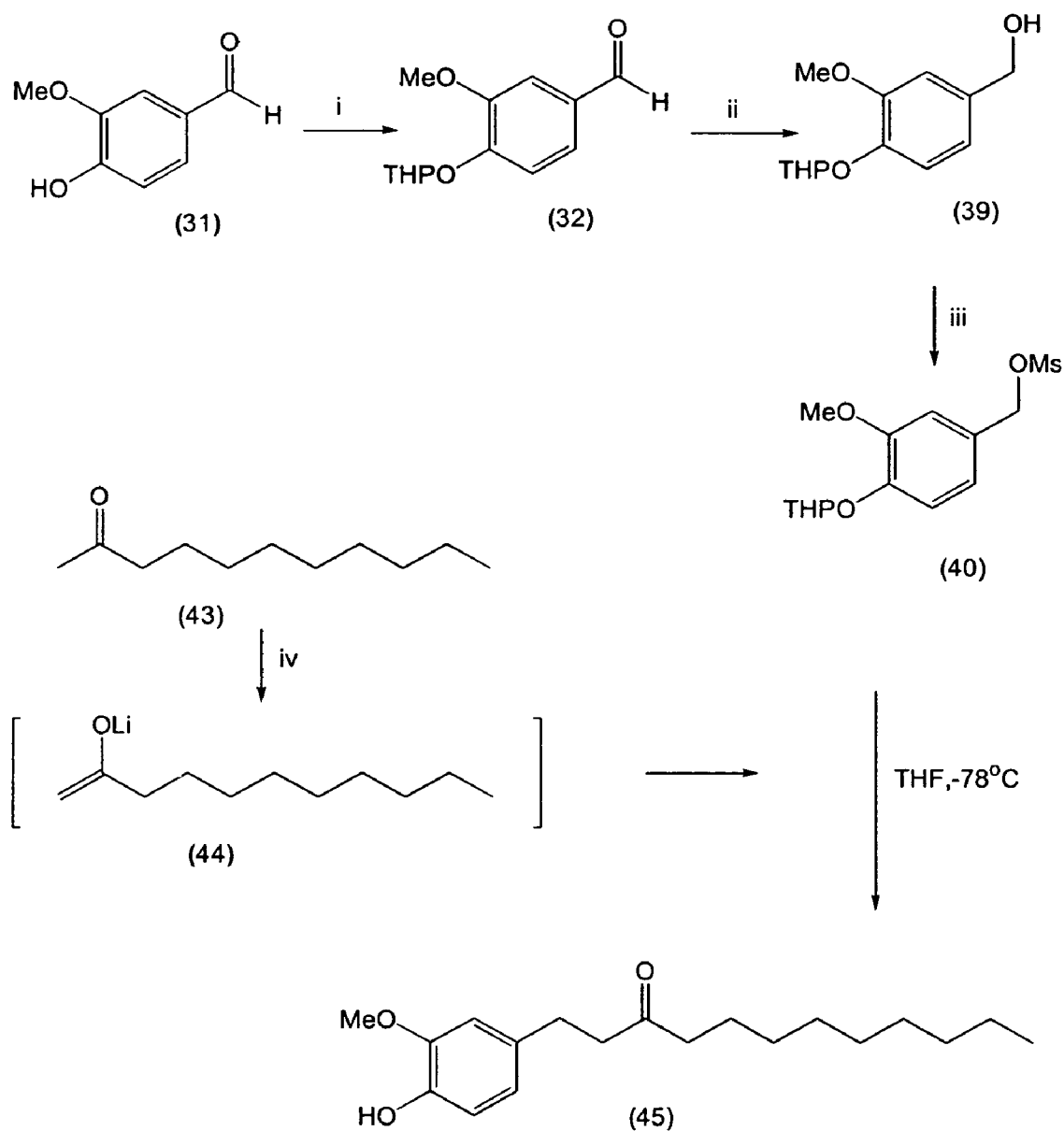
FIG. 8 shows a scheme for the synthesis of [9]-dihydroshogaol, compound (45).

The phenol group of vaniline, compound (31), was protected as the THP ether (DHP/PPTS/CH$_2$Cl$_2$) to yield compound (32), and the aldehyde group of compound (32) was reduced to the alcohol to yield compound (39) using NaBH$_4$ in THF as shown in FIG. 8. The resulting alcohol, compound (39), was mesylated (methanesulfonyl chloride/triethylamine/THF) and reacted with in situ generated lithium 2-undecanonide, compound (44), (2-undecanone/LDA/THF/−78° C.) at −78° C. under N$_2$. The THP ether protecting group was removed by further treating the reaction mixture with PPTS in ethanol at 50° C. to afford [9]-dihydroshogaol, compound (45).

Figure 9:
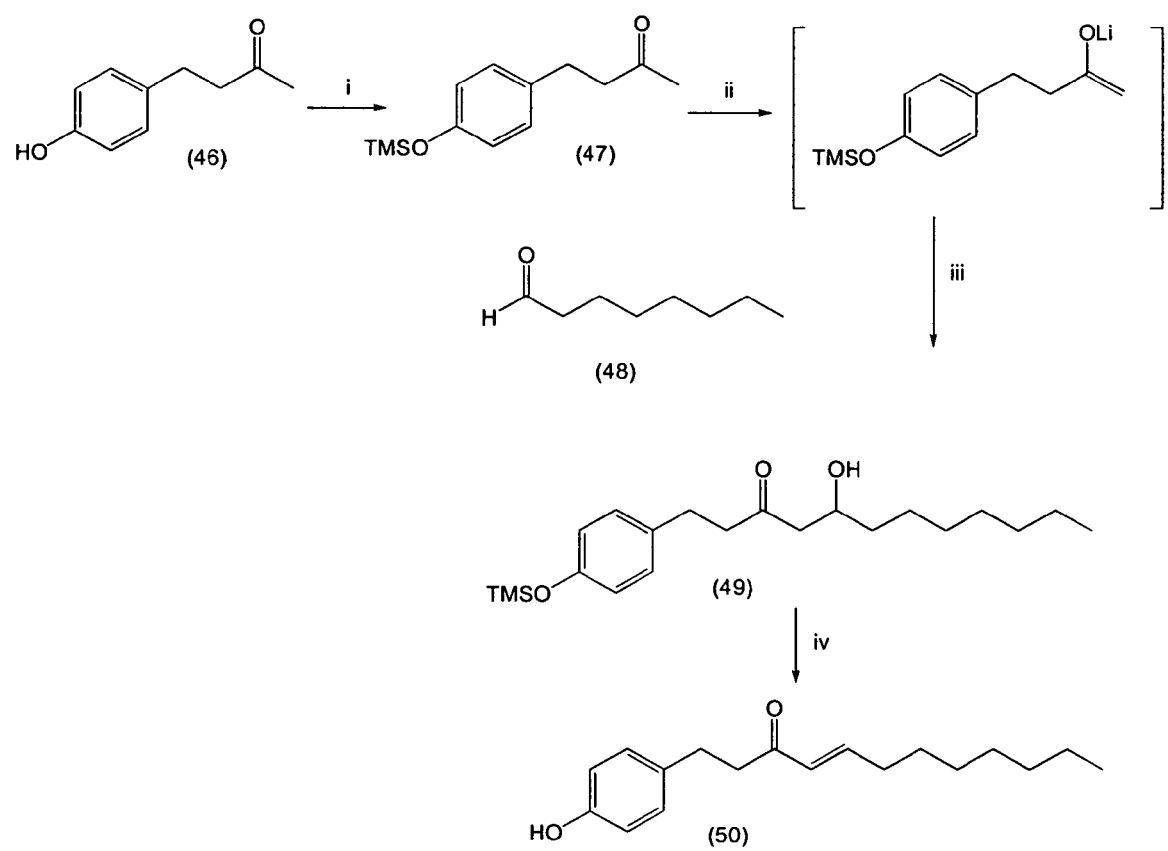
FIG. 9 shows a scheme for the synthesis of [9]-demothoxyshogaol, compound (50).

The phenol group on 4-(4-hydroxy-phenyl)-2-butanone, compound (46), was protected as the TMS ether (TMSCl/triethylamine/THF) at room temperature as shown in FIG. 9. The resulting ketone, compound (47), was reacted with LDA at −78° C. in THF under N$_2$ to generate lithium enolate which was reacted with octyl aldehyde compound (48), to afford the β-hydroxy ketone, compound (49). The TMS group was removed by stirring with NaHCO$_3$ in methanol at room temperature. Dehydration of the β-hydroxy group was achieved by further treatment of the reaction mixture with methanolic HCl (1 N) at room temperature to afford [9]-demethoxyshogaol, compound (50).

EXAMPLE 8

Figure 10:
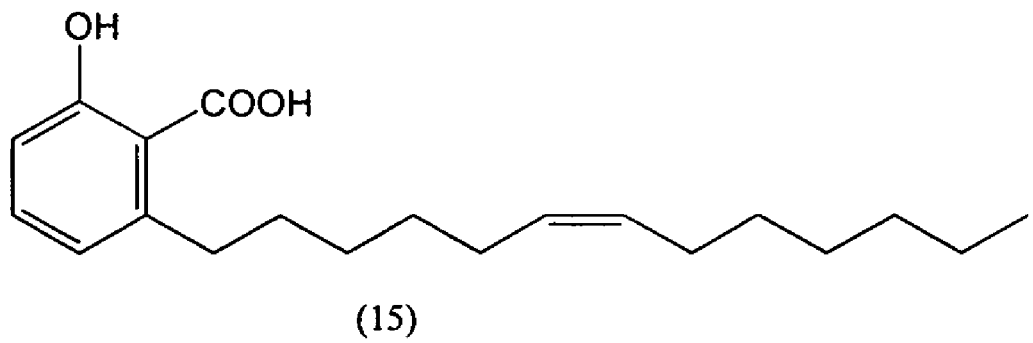
FIG. 10 shows the structures of *ginkgo biloba*-derived natural product compounds that protected PC12 and HUVEC cells from βA peptide-induced toxicity.
Figure 10:
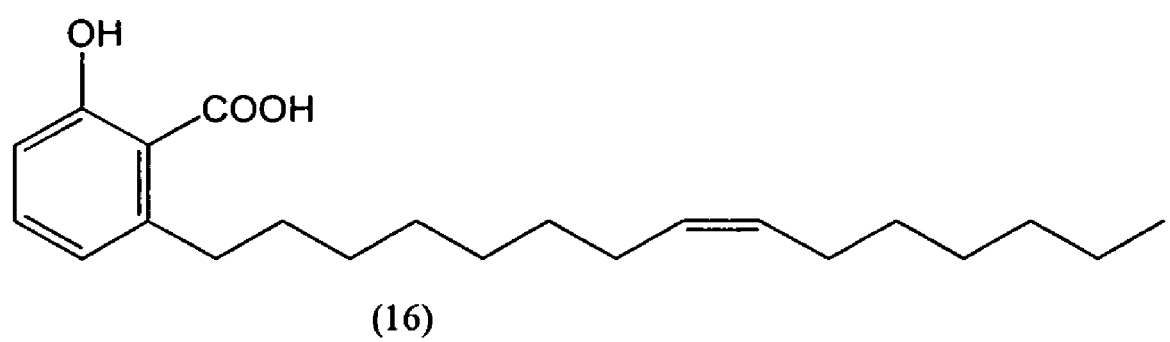

Isolation and Identification of Natural Product Compounds Derived from Gingko Biloba that Protect Cells from Beta Amyloid-Induced Toxicity According to this example, freshly ground fresh ginkgo nuts (1 kg) were extracted with methanol (2×2000 ml) and sequentially partitioned with petroleum ether, ethyl acetate, dichloromethane, and butanol. The petroleum ether and ethyl acetate fractions protected PC12 and HUVEC cells from βA peptide(25-35)-induced cytotoxicity at $ED_{50}$=10 μg/ml. The active principles were isolated from the residues of active fractions by a series of column chromatography using various resins (Amberchrom non-ionic resin and silica gel) and semi-preparative HPLC reverse-phased separation (isopropyl alcohol/water or acetonitrile/water solvent system). The structures of the compounds were elucidated using 1-D and 2-D NMR techniques that include $^1$H, $^{13}$C, HMBC, and APT. Cis conformation of the double bond was unambiguously assigned in the $^1$H NMR spectrum. The position of the double bond was elucidated by oxidatively cleaving it to acid functionality (KMnO$_4$ oxidation) and observing the mass spectral fragmentation pattern (EI 70 eV). The two compounds (15) and (16) have ginkgolic acid structures, and are shown in FIG. 10. These compounds have been previously isolated from ginkgo leaves, See Jaggy et al., *Pharmazie* 52, 735 (1997).

EXAMPLE 9

Inhibitory Activity of *Ginkgo Biloba*-Derived Natural Product Compounds Against Beta Amyloid Toxicity According to this example, the inhibitory activity of natural product compounds derived from *ginkgo biloba* against βA peptide-induced toxicity was measured by MTT reduction assay. The two *ginkgo biloba*-derived natural product compounds that do not possess antioxidant properties, compounds (15) and (16), were found to protect PC12, IMR32, and HUVEC cells from βA peptide-induced toxicity. The results of the MTT assay were confirmed by following the LDH methodology set forth in example 2. This example also provides data indicating that the ginkgolides A, B, and C, (−)bilobalide, and quercetin do not possess biological activity against βA peptide as had been postulated in the prior art.

TABLE 4

Inhibitory Activity of Ginkgolic Acids 1 and 2, Ginkgolide A, Ginkgolide B, Ginkgolide C, (−)-Bilobalide, and Quercetin Toward β- Insult Against PC12, IMR32, and HUVEC Cells.

| Compound | Anti-βA peptide(25-35) $ED_{50}$ (µg/ml) PC12 | Anti-βA peptide(1-42) $ED_{50}$ (µg/ml) PC12 | Anti-βA peptide(25-35) $ED_{50}$ (µg/ml) IMR32 | Anti-βA peptide(1-42) $ED_{50}$ (µg/ml) IMR32 | Anti-βA peptide(25-35) $ED_{50}$ (µg/ml) HUVEC | Anti-βA peptide(1-42) $ED_{50}$ (µg/ml) HUVEC |
|---|---|---|---|---|---|---|
| 15 | 3.0 | 2.0 | 3.5 | 2.5 | 5.0 | 1.5 |
| 16 | 2.0 | 1.0 | 2.0 | 1.0 | 2.5 | 1.0 |
| Ginkgolide A | toxic | toxic | toxic | toxic | toxic | toxic |
| Ginkgolide B | toxic | toxic | toxic | toxic | toxic | toxic |
| Ginkgolide C | toxic | toxic | toxic | toxic | toxic | toxic |
| (−)-Bilobalide | toxic | toxic | toxic | toxic | toxic | toxic |
| Quercetin | >20 | >20 | >20 | >20 | >20 | >20 |

EXAMPLE 10

A Proposed Gingkolic Acid Synthesis

Figure 11:
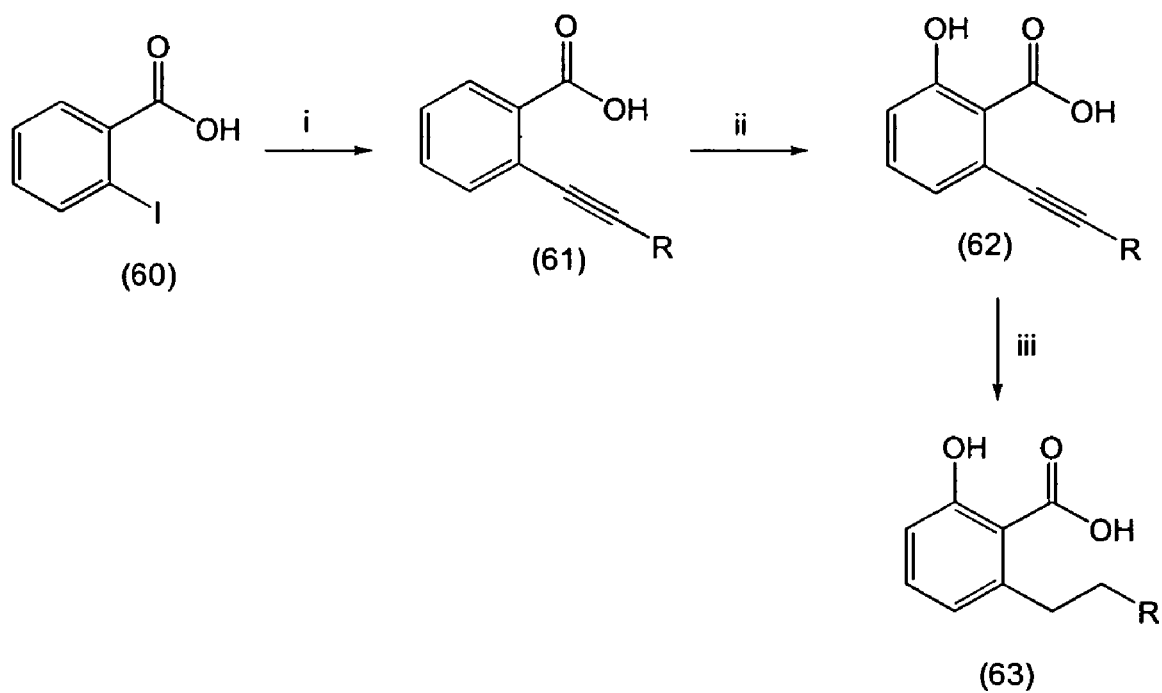
FIG. 11 shows a proposed synthesis for ginkolic acids and their analogues.

According to this example, a gingkolic acid synthesis is proposed as shown in FIG. 11. The benzoic acid, compound (60) and an alkyne having a terminal carbon-carbon triple bond, R, are treated with tetrakis(triphenylphosphine)palladium, in the presence of diisopropyl amine and copper(I) iodide to yield an alkyne substituted benzoic acid, compound (61). Compound (61) is treated with LDA in THF, the temperature is lowered to −78° C. and the reaction mixture is treated with oxodiperoxymolybdenum (pyridine)-(hexamethylphosphoric triamide) (MoOPh) to yield a hydroxy functionalized product, compound (62). Compound (62) is then reacted with hydrogen gas over a palladium/carbon catalyst, and treated with acetic acid to yield the desired ginkgolic acid product, compound (63).

EXAMPLE 11

Control Study

As a control study, vitamin A, β-carotene, vitamin C, and vitamin E were tested for both anti-βA peptide(25-35) and anti-βA peptide(1-42) activity. Since these vitamins are suggested for the delaying the onset of AD, the biological activity of the compounds of the invention were compared with these vitamins. Under the experimental conditions, these vitamins did not protect PC12 cells from βA peptide insults even at 200 µg/ml. Congo red was also tested because it has been reported to inhibit βA peptide fibril-induced toxicity against PC12 cells. At high concentrations of Congo red (>25 µg/ml), the data from the cell viability evaluation using MTT reduction assay was not reliable because of the dye's intense red color. Nevertheless, the natural product compounds (1), (2), (3), and (4) and natural product compounds (11), (12), (13), and (14) ($ED_{50}$=20.0-0.5 µg/ml) are more than 20-40 times as effective in protecting PC12 cells against βA peptide insults when compared with these vitamins and other agents.

EXAMPLE 12

Reduced Glutathione Assisted βA Peptide Toxicity Inhibition Assay

According to this example, the compounds of the invention were evaluated to ascertain if their antioxidant potency was increased when administered in conjunction with reduced glutathione. The synergistic interaction between estrogens and the intracellular antioxidant, reduced glutathione (GSH), was reported to protect neurons from βA peptide-induced toxicity. See Barkats et al., *J Neurochem* 75, 1438 (2000) and Muller et al., *J Neurochem* 68, 2371 (1997). The possible involvement of this mechanism was evaluated using PC12 cells with the compounds of the invention. The dose of GSH used in this study was comparable to the low micromolar GSH (3.25 µM) concentrations found in the cerebrospinal fluid and used by Green et al. It was hypothesized that if the compounds' of the invention ability to protect cells from βA peptide-induced toxicity resulted from the compounds' antioxidant potency, administration of a compound of the invention concurrently with GSH should improve the $ED_{50}$ and $IC_{50}$ values for the compounds. Under the experimental conditions, GSH did not influence the compounds' ability to protect cells from βA peptide insults, and did not enhance the antioxidant potency of the compounds.

EXAMPLE 13

Determination of Ability of Compounds of the Invention to Pass Through the Blood Brain Barrier According to this example, the ability of the compounds of the invention to pass through the blood brain barrier was measured. The ability of compounds to cross the blood brain barrier is represented by the log of the partition coefficient (P) of a molecule of the invention between water and octane alcohol. Natural product compounds (1) and (3) were found to have log P values of 3.4 and 3.1, respectively. Accordingly, the octane alcohol fraction contained more than 1000 times as much of the compounds as the water fraction. These results suggest that the compounds are able to cross the blood brain barrier. See Hau et al., *Regul Toxicol Pharmacol* 35, 273 (2002) and Salminen et al., *J Pharm Biomed Anal* 15, 469 (1997).

Although the present invention has been described in considerable detail with reference to certain preferred embodiments thereof, other versions are possible. Therefore, the spirit and scope of the appended claims should not be limited to the preferred embodiments contained herein.

REFERENCES

Arancio O, Zhang H P, Chen X, Lin C, Trinchese F, Puzzo D, Liu S. Hegde A, Yan S F, Stern A, Luddy J S, Lue L F, Walker D G, Roher A, Buttini M, Mucke L, Li W, Schmidt A M, Kindy M, Hyslop P A, Stern D M, Du Yan S S. (2004) RAGE potentiates Abeta-induced perturbation of neuronal function in transgenic mice. EMBO J. 23:4096-105.

Barger S W, Horster D, Furukawa K, Goodman Y, Krieglstein J, Mattson M P. (1995) Tumor necrosis factors alpha and beta protect neurons against amyloid beta-peptide toxicity: evidence for involvement of a kappa B-binding factor and attenuation of peroxide and Ca2+ accumulation. Proc Natl Acad Sci USA. 92:9328-32.

Barkats M, Millecamps S, Abrioux P, Geoffroy M C, Mallet J. (2000) Overexpression of glutathione peroxidase increases the resistance of neuronal cells to Abeta-mediated neurotoxicity. J. Neurochem. 75:1438-46.

Barik A, Mishra B, Shen L, Mohan H, Kadam R M, Dutta S, Zhang H Y, Priyadarsini K I. (2005) Evaluation of a new copper(II)-curcumin complex as superoxide dismutase mimic and its free radical reactions. Free Radic Biol Med. 39:811-22.

Beard C M, Waring S C, O'Brien P C, Kurland L T, Kokmen E (1998) Nonsteroidal anti-inflammatory drug use and Alzheimer's disease: a case-control study in Rochester, Minn., 1980 through 1984. Mayo Clin Proc 73: 951-955.

Behl C, Davis J, Lesley R, Schubert D (1994) Hydrogen peroxide mediates amyloid β protein toxicity. Cell 77:817-827.

Bressler N M, Gills J P (2000) Age related macular degeneration, BMJ 321, 1425-1427.

Carr D B, Goate A, Morris J C (1997) Current concepts in the pathogenesis of Alzheimer's disease. Am J Med 103:3S-10S.

Chopdar A, Chakravarthy U, Verma D (2003) Age related macular degeneration, BMJ 326, 485-488.

Cuajungco M P, Lees G J (1997) Zinc metabolism in the brain: relevance to human neurodegenerative disorders. Neurobiol Dis 4:137-169.

Davis J, McMurray H, Schubert D (1992) The amyloid β-protein of Alzheimer's disease is chemotactic for monoclonal phagocytes. Biochem Biophys Res Commun 189:1096-1100.

Dentchev T, Milam A H, Lee V M, Trojanowski J Q, Dunaief J L (2003) Amyloid-beta is found in drusen from some age-related macular degeneration retinas, but not in drusen from normal retinas. Mol Vis 14, 184-190.

Frackowiak J, Mazur-Kolecka B, Kaczmarski W, Dickson D. (2001) Deposition of Alzheimer's vascular amyloid-beta is associated with decreased expression of brain L-3-hydroxyacyl-coenzyme A dehydrogenase (ERAB). Brain Res. 907:44-53.

Friedlich A L, Butcher L L (1994) Involvement of free oxygen radicals in β-amyloidosis: An hypothesis. Neurobiol Aging 15:443-55.

Ghanta J, Shen C L, Kiessling L L, Murphy R M (1996) A strategy for disigning inhibitors of β-amyloid toxicity. J. Biol. Chem. 271:29525-29528.

Goedert M (1993) Tau protein and the neurofibrillary pathology of Alzheimer's disease. Trends Neurosci 16:460-465.

Green P S, Gridley K E, Simpkins J W (1998) Nuclear estrogen receptor-independent neuroprotection by estratrienes: a novel interaction with glutathione. Neuroscience 84:7-10.

Haass C, Selkoe D (1994) Cellular processing of β-amyloid precursor protein and the genesis of amyloid β-peptide. Cell 7:1039-1042.

Haraguchi H, Saito T, Okamura N, Yagi A (1995) Inhibition of lipid peroxidation and superoxide generation by diterpenoids from *Rosmarinus officinalis*. Planta Med 61: 333-336.

Harkany T, Lengyel Z, Soos K, Penke B, Luiten P G, Gulya K (1995) Cholinotoxic effects of β-amyloid (1-42) peptide on cortical projections of the rat nucleus basalis magnocellularis. Brain Res 695:71-75.

Hau K M, Connell D W, Richardson B J. (2002) A study of the biological partitioning behavior of n-alkanes and n-alkanols in causing anesthetic effects. Regul Toxicol Pharmacol. 35: 273-9.

Hefti F (1994) Development of effective therapy for Alzheimer's disease based on neurotrophic factors. Neurobiol Aging 15 (Suppl 2):S193-194.

Henderson V W (1997) The epidemiology of estrogen replacement therapy and Alzheimer's disease. Neurology 48 (5 Suppl. 7):S27-S35.

Hensley K, Carney J M, Mattson M P, Aksenova M, Harris M, Wu J F, Floyd R A, Butterfield D A (1994) A model for β-amyloid aggregation and neurotoxicity based on free radical generation by the peptide: Relevance to Alzheimer's disease. Proc Natl Acad Sci USA 91:3270-3274.

Hertel C, Terzi E, Hauser N, Jakob-Rotne R, Seelig J, Kemp J A (1997) Inhibition of the electrostatic interaction between β-amyloid peptide and membrane prevents β-amlyoid-induced toxicity. Proc Natl Acad Sci USA 94:9412-9416.

Hidalgo P J, Ubera J L, Tena M T, Valcarcel M (1998) Determination of the camosic acid content in wild and cultivated *Rosmarinus officinalis*. J Agric Food Chem 46:2624-2627.

Hopia A I, Huang S W, Schwarz K, German J B, Frankel E N (1996) Effect of different lipid system on antioxidant activity of rosemary constituents carnosol and carnosic acid with and without α-tocopherol. J Agric Food Chem 44:2030-2036.

Hoshi M, Takashima A, Murayama M, Yasutake K, Yoshida N, Ishiguro K, Hoshino T, Imahori K (1997) Nontoxic amyloid β peptide 1-42 suppresses acetylcholine synthesis. Possible role in cholinergic dysfunction in Alzheimer's disease. J Biol Chem 272:2038-2041.

Huttunen H J, Fages C, Rauvala H. (1999) Receptor for advanced glycation end products (RAGE)-mediated neurite outgrowth and activation of NF-kappaB require the cytoplasmic domain of the receptor but different downstream signaling pathways. J Biol Chem. 274:19919-24.

Ihara Y, Nukina N, Miura R, Ogawara M (1986) Phosphorylated tau protein is integrated into paired helical filaments in Alzheimer's disease. J Biochem 99:1807-1810.

Inatani R, Nakatani N, Fuwa H (1983) Antioxidative effect of the constituents of rosemary (*Rosmarinus officinalis* L.) and their derivatives. Agric Biol Chem 47: 521-528. Nakatani N, Inatani R (1984) Two antioxidative diterpenes from rosemary (*Rosmarinus officinalis* L.) and a revised structure for rosmanol. Agric Biol Chem 48: 2081-2085.

Inatani R, Nakatani N, Fuwa H, Seto H (1982) Structure of a new antioxidative phenolic diterpene isolated from rosmary (*Rosmarinus officinalis* L.) Agric Biol Chem 46: 1661-1666.

Ioudina M, Uemura E. (2003) A three amino acid peptide, Gly-Pro-Arg, protects and rescues cell death induced by amyloid beta-peptide. Exp Neurol. 184:923-9.

Jaggy H, Koch E. (1997) Chemistry and Biology of alkylphenols from *Ginkgo biloba* L. Parmazie 52: 735-738

Jitoe A, Masuda T, Tengah I G P, Suprapta D N, Gara I W, Nakatani N (1992) Antioxidant activity of tropical ginger extracts and analysis of the contained curcumoids. J Agric Food Chem 40:1337.

Johnson L V, Leitner W P, Rivest A J, Staples M K, Radeke M J, Anderson D H (2002) The Alzheimer's A beta-peptide is deposited at sites of complement activation in pathologic deposits associated with aging and aging-related macular degeneration. Proc Natl Acad Sci. USA 99,11830-11835.

Khaw P T, Cordeiro M F (2000) Towards better treatment of glaucoma, BMJ 320, 1619-1620.

Khaw P T, Shah P, Elkington A R (2004) Glaucoma-2: Treatment, BMJ 328, 156-158.

Kihara T, Shimohama S, Urushitani M, Sawada H, Kimura J. Kume T, Maeda T, Akaike A (1998) Stimulation of $\alpha 4\beta 2$ nicotinic acetylcholine receptors inhibits $\beta$-amyloid toxicity. Brain Res 792:331-334.

Kikuzaki H, Nakatani N (1993) Antioxidant effects of some ginger constituents. J. Food Sci 58:1407-1410.

Kim D S H L, Park S Y, Kim J Y (2001) Curcuminoids from *Curcuma longa* L. (Zingiberaceae) that protect PC12 rat pheochromocytoma and normal human umbilical vein endothelial cells from $\beta A(1-42)$ insult. Neurosci Lett 303: 57-61.

Kim D S H L, Kim D S, Oppel M N (2002) Shogaols from *Zingiber officinale* L. (Zingiberaceae) Protect IMR32 Human Neuroblastoma and Normal Human Umbilical Vein Endothelial Cells from $\beta$-Amyloid(25-35) Insult. Planta Medica 68:375-376.

Kimura M, Akasofu S, Ogura H, Sawada K. (2005) Protective effect of donepezil against Abeta(1-40) neurotoxicity in rat septal neurons. Brain Res. 1047:72-84.

Klegeris A, Walker D, Mcgeer P L (1994) Activation of macrophages by Alzheimer $\beta$-amyloid peptide. Biochem Biophys Res Commun 199:984-991.

Kumar U, Dunlop D M, Richardson J S (1994) The acute neurotoxic effect of $\beta$-amyloid on mature cultures of rat hippocampal neurons is attenuated by the anti-oxidant U-78517F. Int J Neurosci 79:185-190.

Lahiri D K, Lewis S, Farlow M R (1994) Tacrine alters the secretion of the $\beta$-amyloid precursor protein in cell lines. J Neurosci Res 37:777-787.

Lorenzo A, Yankner B A (1996) Amyloid fibril toxicity in Alzheimer's disease and diabetes. Ann NY Acad Sci 777: 89-95.

Lucca E, Angeretti N, Forloni G (1997) Influence of cell culture conditions on the protective effects of antioxidants against $\beta$-amyloid toxicity: studies with lazaroids. Brain Res 764:293-298.

Manelli A M, Puttfarcken P S (1995) $\beta$-Amyloid-induced toxicity in rat hippocampal cells: in vitro evidence for the involvement of free radicals. Brain Res Bull 38:569-76.

Mattson M P (1997) Neuroprotective signal transduction: relevance to stroke. Neurosci Biobehav Rev 21:193-206.

Maurice T, Lockhart B P, Privat A (1996) Amnesia induced in mice by centrally administered $\beta$-amyloid peptides involves cholinergic dysfunction. Brain Res 706:181-193.

McCarty C A, Mukesh B N, Fu C L, Mitchell P, Wang J J, Taylor H R (2001) Risk factors for age-related maculopathy: The visual impairment project. Arch Ophthalmol 119, 1455-1462.

McKinnon S J, Lehman D M, Kerrigan-Baunrind L A, Merges C A, Pease M E, Kerrigan D F, Ransom N L, Tahzib N G, Reitsamer H A, Levkovitch-Verbin H, Quigley H A, Zack D J (2002) Caspase activation and amyloid precursor protein cleavage in rat ocular hypertension, IOVS 43,1077-1087.

Meda L, Cassatella M A, Szendrei G I, Otvos L Jr, Baron P, Villalba M, Ferrari D, Rossi F (1995) Activation of microglial cells by $\beta$-amyloid protein and interferon-$\gamma$. Nature 374:647-650.

Muller W E, Romero F J, Perovic S, Pergande G, Pialoglou P (1997) Protection of flupirtine on $\beta$-amyloid-induced apoptosis in neuronal cells in vitro: prevention of amyloid-induced glutathione depletion. J Neurochem 68:2371-2377.

Nakatani N, Inatani R (1983) A new diterpene lactone, rosmadial, from rosemary (*Rosmarinus officinalis* L.). Agric Biol Chem 47:353-358.

Nurfina A N, Reksohadiprodjo M S, Timmerman H, Jenie U A, Sugiyanto H, van der Goot H (1997) Synthesis of some symmetrical curcumin derivatives and their antiinflammatory activity. Eur J Med Chem 32:321-328.

Park S Y, Kim D S H L (2002) Discovery of natural products from *Curcuma longa* L. (Zingiberaceae) that protect cells from beta-amyloid insult: a drug discovery effort against Alzheimer's disease. J Nat Prod 65:1227-1231.

Pametti L, Senin U, Mecocci P (1997) Cognitive enhancement therapy for Alzheimer's disease. The way forward. Drugs 53:752-768.

Pasinetti G M, Aisen P S (1998) Cyclooxygenase-2 expression is increased in frontal cortex of Alzheimer's disease brain. Neuroscience 87:319-324.

Perini G, Della-Bianca V, Politi V, Della Valle G, Dal-Pra I, Rossi F, Armato U. (2002) Role of p75 neurotrophin receptor in the neurotoxicity by beta-amyloid peptides and synergistic effect of inflammatory cytokines. J Exp Med. 195: 907-18.

Pike C J, Burdick D, Walencewicz A J, Glabe C G, Cotman C W (1993) Neurodegeration induced by $\beta$-amyloid peptides in vitro: the role of peptide assembly state. Neuroscience 13:1676-1687.

Pike C J, Ramezan-Arab N, Cotman C W (1997) $\beta$-Amyloid neurotoxicity in vitro: evidence of oxidative stress but not protection by antioxidants. J Neurochem 69:1601-1611.

Pollack S J, Sadler I I, Hawtin S R, Tailor V J, Shearman M S (1995) Sulfonated dyes attenuate the toxic effects of $\beta$-amyloid in a structure-specific fashion. Neurosci Lett 197:211-214.

Preston J E, Hipkiss A R, Himsworth D T, Romero I A, Abbott J N (1998) Toxic effects of $\alpha$-amyloid(25-35) on immortalised rat brain endothelial cell: protection by carnosine, homocarnosine and $\beta$-alanine. Neurosci Lett 242:105-108.

Puttfarcken P S, Manelli A M, Neilly J, Frail D E (1996) Inhibition of age-induced $\beta$-amyloid neurotoxicity in rat hippocampal cells. Exp Neurol 138:73-81.

Ruby A J, Kuttan G, Babu K D, Rajasekharan K N, Kuttan R (1995) Anti-tumour and antioxidant activity of natural curcuminoids. Cancer Lett 94:79-83.

Salminen T, Pulli A, Taskinen J. (1997) Relationship between immobilised artificial membrane chromatographic retention and the brain penetration of structurally diverse drugs. J Pharm Biomed Anal. 15:469-77.

Schulick P (1994) Ginger: common spice and wonder drug; Herbal Free Press, Ltd. Brattleboro, Vt.

Seidl R, Schuller E, Cairns N, Lubec G (1997) Evidence against increased glycoxidation in patients with Alzheimer's disease. Neurosci Lett 232:49-52.

Seiger A, Nordberg A, von Holst H, Backman L, Ebendal T, Alafuzoff I, Amberla K, Hartvig P, Herlitz A, Lilja A, Lundqvist H, Langstrom B, Meyerson B, Persson A, Viitanen M, Winblad B, Olson L (1993) intracranial infusion of purified nerve growth factor to an Alzheimer patient: the first attempt of a possible future treatment strategy. Behav Brain Res 57:255-261.

Shastry B S (1998) Molecular genetics of familial Alzheimer disease. Am J Med Sci 315:266-272.

Smith W, Assink J, Klein R, Mitchell P, Klayer C C W, Klein B E K, Hofman A, Jensen S, Wang J J, dejong P T V M (2001) Risk factors for age-related macular degeneration: Pooled findings from three continents. Ophthalmol 108, 697-704.

St George-Hyslop P H, Westaway D A (1999) Antibody clears senile plaques. Nature 400:116-117.

Tarkowski E, Liljeroth A M, Nilsson A, Ricksten A, Davidsson P, Minthon L, Blennow K. (2000) TNF gene polymorphism and its relation to intracerebral production of TNFalpha and TNFbeta in AD. Neurology. 54:2077-81.

Tatton W G, Chalmers-Redman R M (1996) Modulation of gene expression rather than monoamine oxidase inhibition: (−)-deprenyl-related compounds in controlling neurodegeneration. Neurology 47:S171-S183.

Thomas T, Thomas G, McLendon C, Sutton T, Mullan M (1996) β-Amyloid-mediated vasoactivity and vascular endothelial damage. Nature (London) 380:168-71.

Trojanowski J Q, Lee V M-Y (1995) Phosphorylation of paired helical filament tau in Azheimer's disease neurofibrillary lesions: focusing on phosphatases. FASEB J 9:1570-1576.

Trojanowski J Q, Lee V M (1994) Paired helical filament tau in Alzheimer's disease. The kinase connection. Am J Pathol 144:449-453.

VanNewkirk M R, Weih L, McCarty C A, Taylor H R (2001) Cause-specific prevalence of bilateral visual impairment in Victoria, Australia: The visual impairment project. Ophthalmol 108, 960-967.

Yaar M, Zhai S, Pilch P F, Doyle S M, Eisenhauer P B, Fine R E, Gilchrest B A (1997) Binding of β-amyloid to the p75 neurotrophin receptor induces apoptosis. A possible mechanism for Alzheimer's disease. J Clin Invest 100: 2333-2340.

Yan S D, Chen X, Fu J, Chen M, Zhu H, Roher A, Slattery T, Zhao L, Nagashima M, Morser J, Migheli A, Nawroth P, Stern D, Schmidt A M (1997) RAGE and amyloid-β peptide neurotoxicity in Alzheimer's disease. Nature 382:685-691.

Yan S D, Shi Y, Zhu A, Fu J, Zhu H, Zhu Y, Gibson L, Stern E, Collison K, Al-Mohanna F, Ogawa S, Roher A, Clarke S G, Stern D M. (1999) Role of ERAB/L-3-hydroxyacyl-coenzyme A dehydrogenase type II activity in Abeta-induced cytotoxicity. J Biol. Chem. 274:2145-56.

Wang M, Li J, Rangarajan M, Shao Y, LaVoie E J, Huang T-C, Ho C-T (1998) Antioxidative phenolic compounds from Sage (Salvia officinalis) J Agric Food Chem 46: 4869-4873.

Wang M, Shao Y, Huang T-C, Wei G-J, Ho C-T (1998) Isolation and structural elucidation of aroma constituents bound as glycosides from Sage (Salvia officinalis) J Agric Food Chem 46:2509-2511.

Zhang Y, Hong Y, Bounhar Y, Blacker M, Roucou X, Tounekti 0, Vereker E, Bowers W J, Federoff H J, Goodyer C G, LeBlanc A. (2003) p75 neurotrophin receptor protects primary cultures of human neurons against extracellular amyloid beta peptide cytotoxicity. J Neurosci. 23:7385-94.

Zhou Y, Gopalakrishnan V, Richardson J S (1996) Actions of neurotoxic β-amyloid on calcium homeostasis and viability of PC12 cells are blocked by antioxidants but not by calcium channel antagonists. J Neurochem 67:1419-1425.

What is claimed is:

1. A method for the treatment of a beta-Amyloid protein-induced ocular disease comprising administering to a subject suffering from a beta-Amyloid protein induced ocular disease a therapeutically effective amount of a composition comprising a member selected from a)

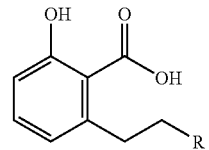

(IV)

or a pharmaceutically acceptable salt or ester thereof, wherein:

R is selected from the group consisting of higher alkyl, higher alkenyl, and higher alkynyl.

2. The method according to claim 1 wherein: R is

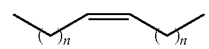

and n is 1-7, and double line is optionally a single bond, a double bond (cis or trans), or a triple bond, or having more than one double or triple bond And R is also selected from the group consisting of alkyl, alkenyl, and alkynyl;

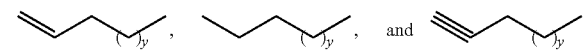

and y is 1-9, or having more than one double bond (cis or trans), or triple bond consisting of;

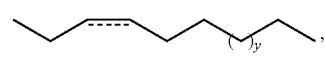

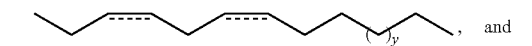

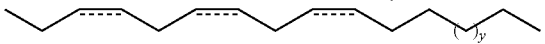

wherein the dotted line configuration is optionally a single bond (cis or trans), or a triple bond, wherein the alkyl, alkenyl, and alkynyl group is selected from ethers and/or thioethers or amines;

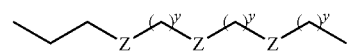

wherein $Z=O$, $S$, $NR_n$, where R=alkyl, alkenyl, alynyl groups; and n=1 or 2.

3. A method for the treatment of a beta-Amyloid protein-induced ocular disease comprising administering to a subject suffering from the beta-Amyloid protein-induced ocular disease a therapeutically effective amount of a compound having a formula (VI):

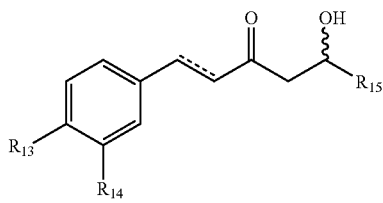

(VI)

or a pharmaceutically acceptable salt or ester thereof, wherein:

the dotted configuration - - - - is optionally a single bond or a double bond or a triple bond;

$R_{13}$ is selected from the group consisting of OH, OMe, OR', and X wherein R' is alkyl, alkenyl, or alkynyl, and X is F, Cl, Br, or I;

$R_{14}$ is selected from the group consisting of H, OH, OMe, and OR' wherein R' is alkyl, alkenyl, or alkynyl; and $R_{15}$ is selected from the group consisting of alkyl, alkenyl, and alkynyl;

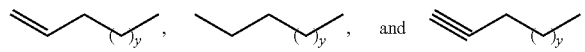

and y is 1-9, or having more than one double bond (cis or trans), or triple bond consisting of;

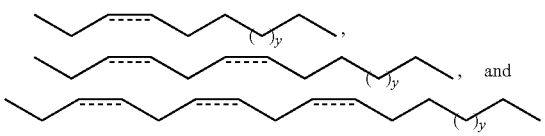

wherein the dotted line configuration is optionally a single bond (cis or trans), or a triple bond, wherein the alkyl, alkenyl, and alkynyl group is selected from ethers and/or thioethers or amines;

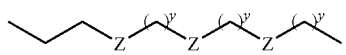

wherein Z=O, S, $NR_n$, where R=alkyl, alkenyl, alynyl groups; and n=1 or 2.

4. The method of claim 1 wherein the composition further comprises one or more ingredients selected from the group consisting of cholinergic agents, oral carbonic anhydrase inhibitors, alpha-2 adrenergic agonists, prostaglandin agonists, carotenoids, lutein and zeaxanthin.

5. The method of claim 3 wherein the composition further comprises one or more ingredients selected from the group consisting of cholinergic agents, oral carbonic anhydrase inhibitors, alpha-2 adrenergic agonists, prostaglandin agonists, carotenoids, lutein and zeaxanthin.

* * * * *